US012185743B2

(12) United States Patent
Abelyan et al.

(10) Patent No.: US 12,185,743 B2
(45) Date of Patent: Jan. 7, 2025

(54) PROCESSES FOR TRANSGLUCOSYLATION OF STEVIOL GLYCOSIDES

(71) Applicant: Beijing Gingko-Group Biological Technology Co., Ltd., Beijing (CN)

(72) Inventors: Varuzhan Abelyan, Moscow (RU); Chunhua Li, Beijing (CN); Yanmei Li, Beijing (CN); Xiangang Lyu, Beijing (CN); Yang Zhang, Beijing (CN); Chunguang Dong, Beijing (CN)

(73) Assignee: Beijing Gingko-Group Biological Technology Co., Ltd., Beijing (CN)

( * ) Notice: Subject to any disclaimer, the term of this patent is extended or adjusted under 35 U.S.C. 154(b) by 995 days.

(21) Appl. No.: 17/269,541

(22) PCT Filed: Jan. 17, 2019

(86) PCT No.: PCT/CN2019/072212
§ 371 (c)(1),
(2) Date: Feb. 19, 2021

(87) PCT Pub. No.: WO2020/147080
PCT Pub. Date: Jul. 23, 2020

(65) Prior Publication Data
US 2021/0329954 A1 Oct. 28, 2021

(51) Int. Cl.
| | |
|---|---|
| A23L 27/30 | (2016.01) |
| A23C 9/13 | (2006.01) |
| A23L 2/60 | (2006.01) |
| B01D 15/20 | (2006.01) |
| B01D 15/42 | (2006.01) |
| C07H 15/24 | (2006.01) |

(52) U.S. Cl.
CPC ............ *A23L 27/36* (2016.08); *A23C 9/1307* (2013.01); *A23L 2/60* (2013.01); *B01D 15/203* (2013.01); *B01D 15/206* (2013.01); *B01D 15/426* (2013.01); *C07H 15/24* (2013.01); *A23V 2002/00* (2013.01)

(58) Field of Classification Search
CPC ......... A23L 27/36; A23L 2/60; A23C 9/1307; B01D 15/203; B01D 15/206; B01D 15/426; C07H 15/24; A23V 2002/00
See application file for complete search history.

(56) References Cited

U.S. PATENT DOCUMENTS

| | | |
|---|---|---|
| 4,219,571 A | 8/1980 | Miyake |
| 2007/0082102 A1 | 4/2007 | Magomet et al. |
| 2010/0166679 A1 | 7/2010 | Abelyan et al. |
| 2010/0189861 A1 | 7/2010 | Abelyan et al. |
| 2012/0214751 A1* | 8/2012 | Markosyan ............. C12P 19/56 514/23 |
| 2013/0287894 A1 | 10/2013 | Markosyan |
| 2014/0017378 A1* | 1/2014 | Purkayastha ........... A23L 27/33 426/442 |

(Continued)

FOREIGN PATENT DOCUMENTS

| | | |
|---|---|---|
| CN | 1390947 A | 1/2003 |
| CN | 1408262 A | 4/2003 |

(Continued)

*Primary Examiner* — Anthony J Weier
(74) *Attorney, Agent, or Firm* — Samson G. Yu

(57) ABSTRACT

A process for transglucosylation of steviol glycosides. A sweetener composition having at least 95% total glycosylated steviol glycosides.

23 Claims, 10 Drawing Sheets

(56) References Cited

U.S. PATENT DOCUMENTS

| | | | | |
|---|---|---|---|---|
| 2014/0227421 A1* | 8/2014 | Markosyan | ............... | A21D 2/36 |
| | | | | 426/583 |
| 2019/0297932 A1* | 10/2019 | Fletcher | ......... | C12Y 204/01019 |
| 2020/0345049 A1* | 11/2020 | Galano | ................... | A23L 27/34 |
| 2024/0148036 A1* | 5/2024 | Markosyan | ............ | A21D 13/04 |

FOREIGN PATENT DOCUMENTS

| CN | 105899087 A | 8/2016 |
|---|---|---|
| CN | 107532189 A | 1/2018 |

* cited by examiner

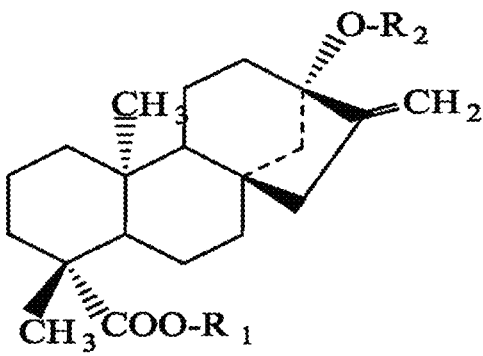

| Compound name | $R_1$ (C-19) | $R_2$ (C-13) |
|---|---|---|
| 1. Steviol | H | H |
| 2. Steviolmonoside | H | β-Glc |
| 3. Rubusoside | β-Glc | β-Glc |
| 4. Steviolbioside | H | β-Glc-β-Glc(2→1) |
| 5. Stevioside | β-Glc | β-Glc-β-Glc(2→1) |
| 6. Rebaudioside A | β-Glc | β-Glc-β-Glc(2→1)<br>      \|<br>   β-Glc(3→1) |
| 7. Rebaudioside B | H | β-Glc-β-Glc(2→1)<br>      \|<br>   β-Glc(3→1) |
| 8. Rebaudioside C | β-Glc | β-Glc-α-Rha(2→1)<br>      \|<br>   β-Glc(3→1) |
| 9. Rebaudioside D | β-Glc-β-Glc(2→1) | β-Glc-β-Glc(2→1)<br>      \|<br>   β-Glc(3→1) |
| 10. Rebaudioside E | β-Glc-β-Glc(2→1) | β-Glc-β-Glc(2→1) |
| 11. Rebaudioside F | β-Glc | β-Glc-β-Xyl(2→1)<br>      \|<br>   β-Glc(3→1) |
| 12. Dulcoside A | β-Glc | β-Glc-α-Rha(2→1) |

FIG. 1

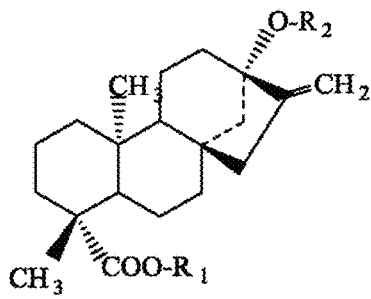

| Compound name | R₁ (C-19) | R₂ (C-13) |
|---|---|---|
| 13. Dulcoside B | H | β-Glc-α-Rha(2→1)<br>    │<br>β-Glc(3→1) |
| 14. Rebaudioside G | β-Glc | β-Glc-β-Glc(3→1) |
| 15. Rebaudioside I | β-Glc-β-Glc(3→1) | β-Glc-β-Glc(2→1)<br>    │<br>β-Glc(3→1) |
| 16. Rebaudioside H | β-Glc | β-Glc-α-Rha(2→1)-β-Glc(3→1)<br>    │<br>β-Glc(3→1) |
| 17. Rebaudioside L | β-Glc | β-Glc-β-Glc(2→1)⎤<br>    │           ⎥ β-Glc(6→1)<br>β-Glc(3→1)  ⎦ |
| 18. Rebaudioside K | β-Glc-β-Glc(2→1) | β-Glc-α-Rha(2→1)<br>    │<br>β-Glc(3→1) |
| 19. Rebaudioside J | β-Glc-α-Rha(2→1) | β-Glc-β-Glc(2→1)<br>    │<br>β-Glc(3→1) |
| 20. Rebaudioside M | β-Glc-β-Glc(2→1)<br>    │<br>β-Glc(3→1) | β-Glc-β-Glc(2→1)<br>    │<br>β-Glc(3→1) |
| 21. Rebaudioside N | β-Glc-α-Rha(2→1)<br>    │<br>β-Glc(3→1) | β-Glc-β-Glc(2→1)<br>    │<br>β-Glc(3→1) |
| 22. Rebaudioside O | β-Glc-α-Rha(2→1)-β-Glc(3→1) | β-Glc-β-Glc(2→1)<br>    │<br>β-Glc(3→1) |

FIG 1 (cont'd)

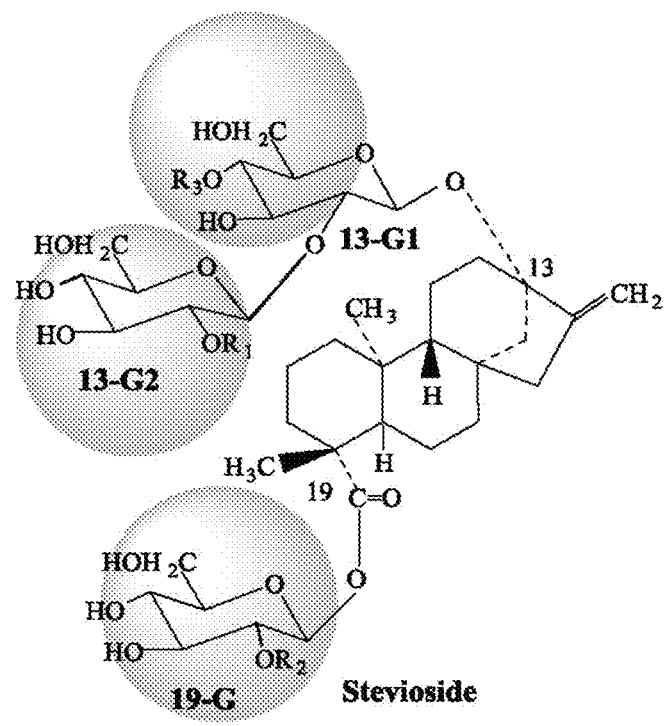
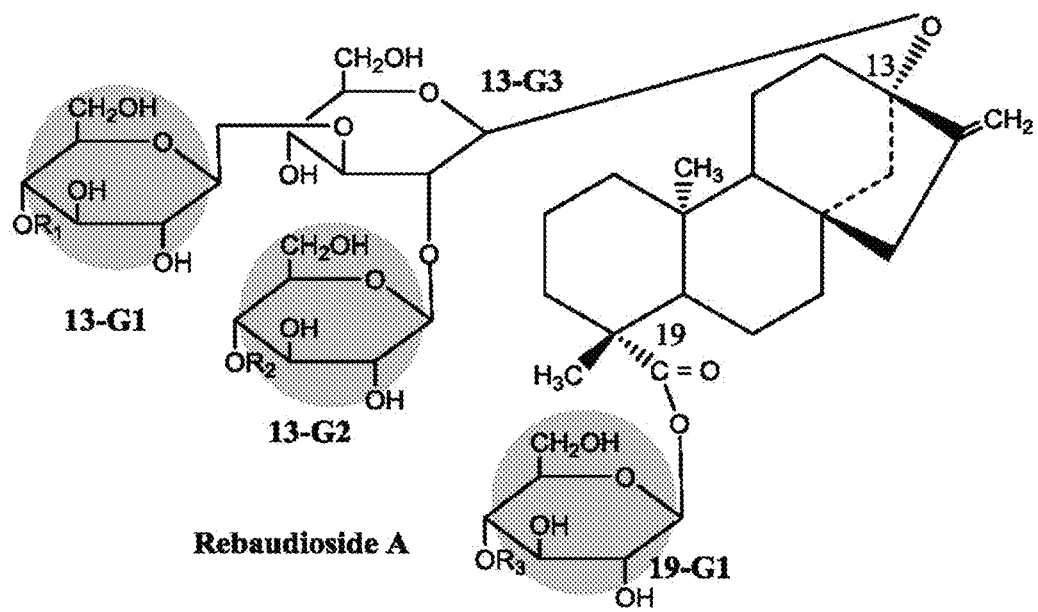
FIG. 2

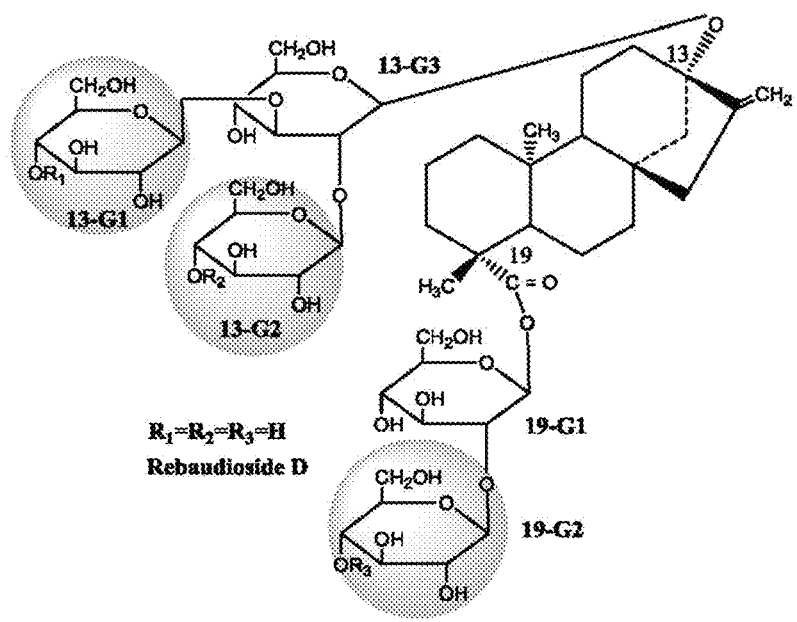
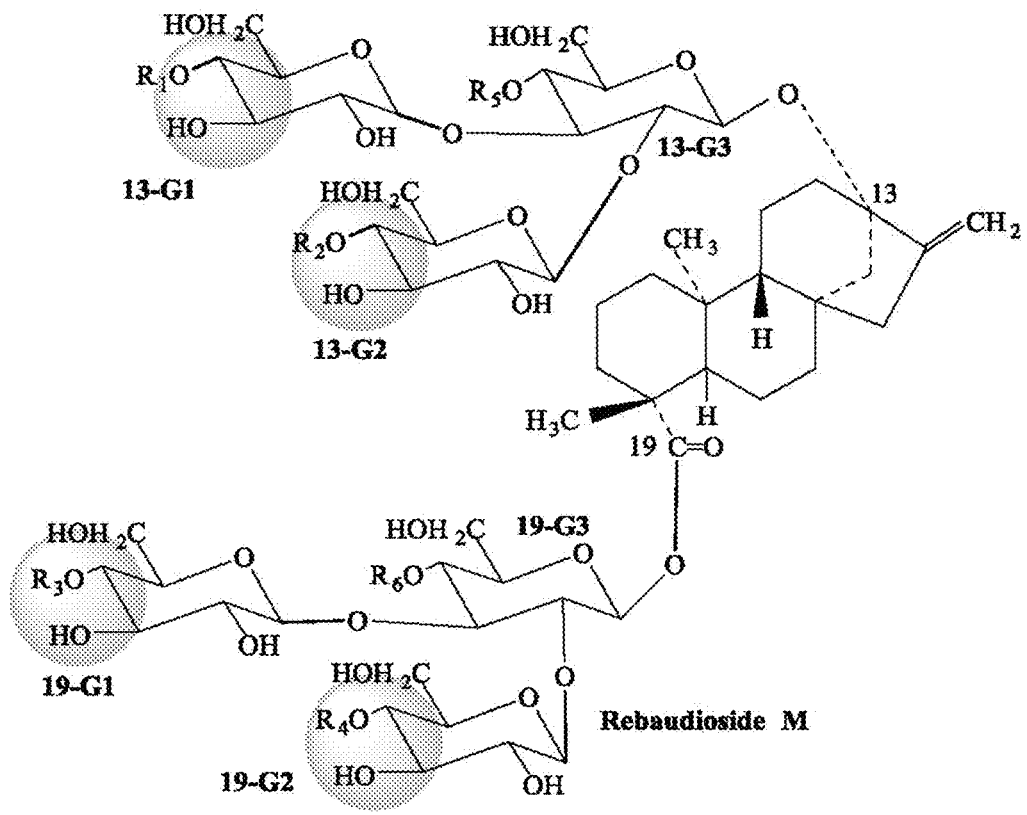
FIG. 2 (cont' d)

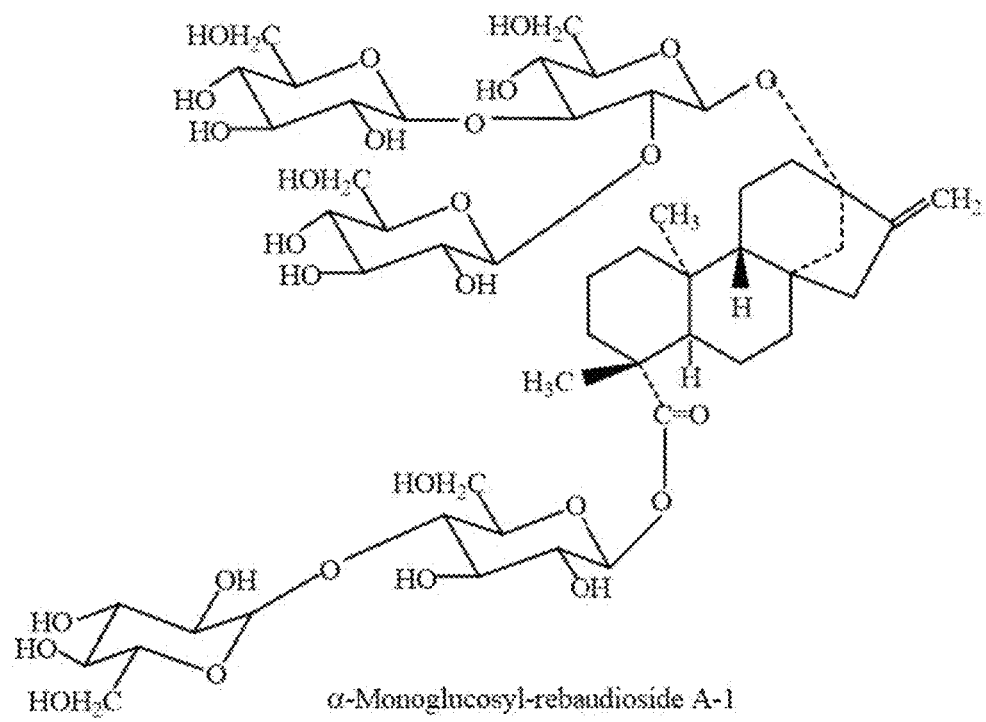
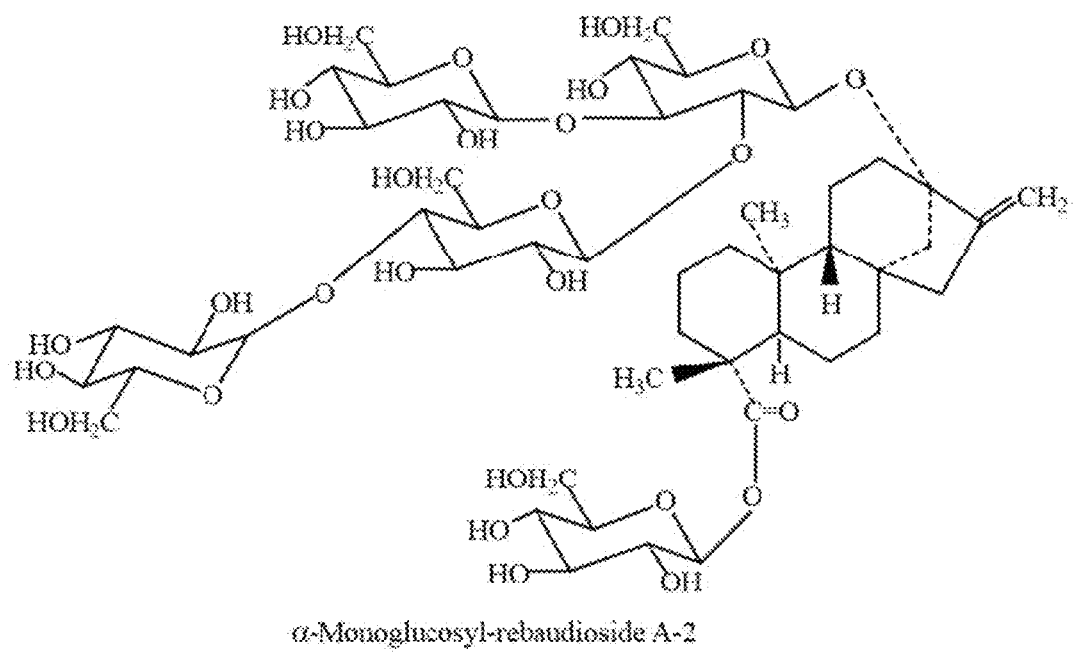
FIG. 3

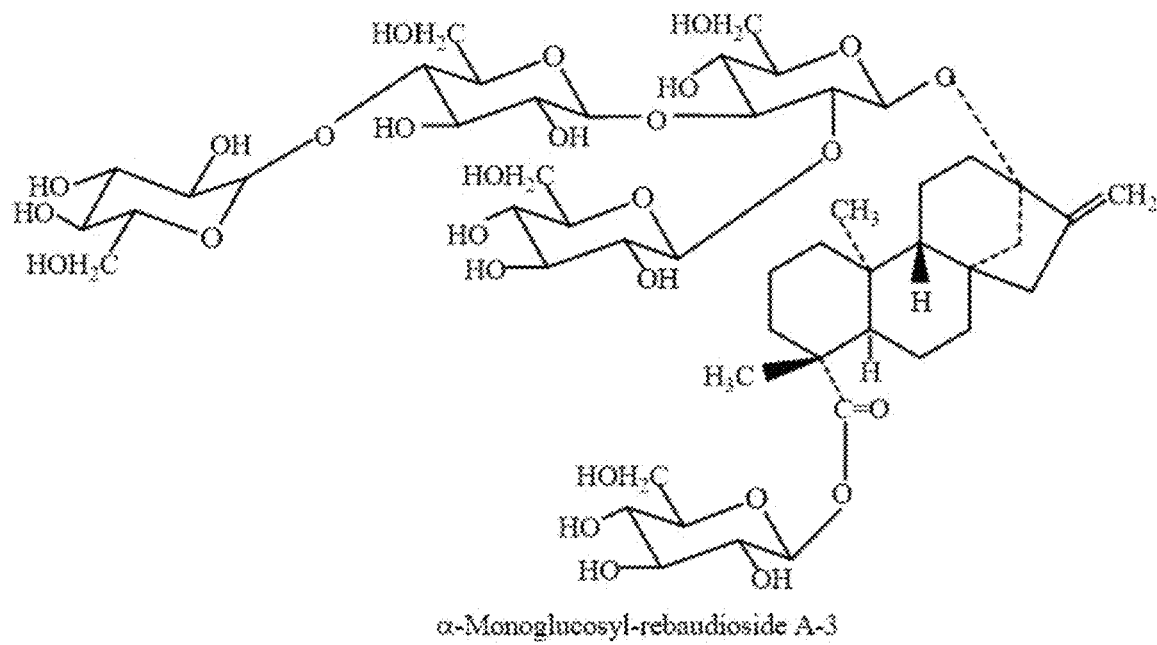
α-Monoglucosyl-rebaudioside A-3
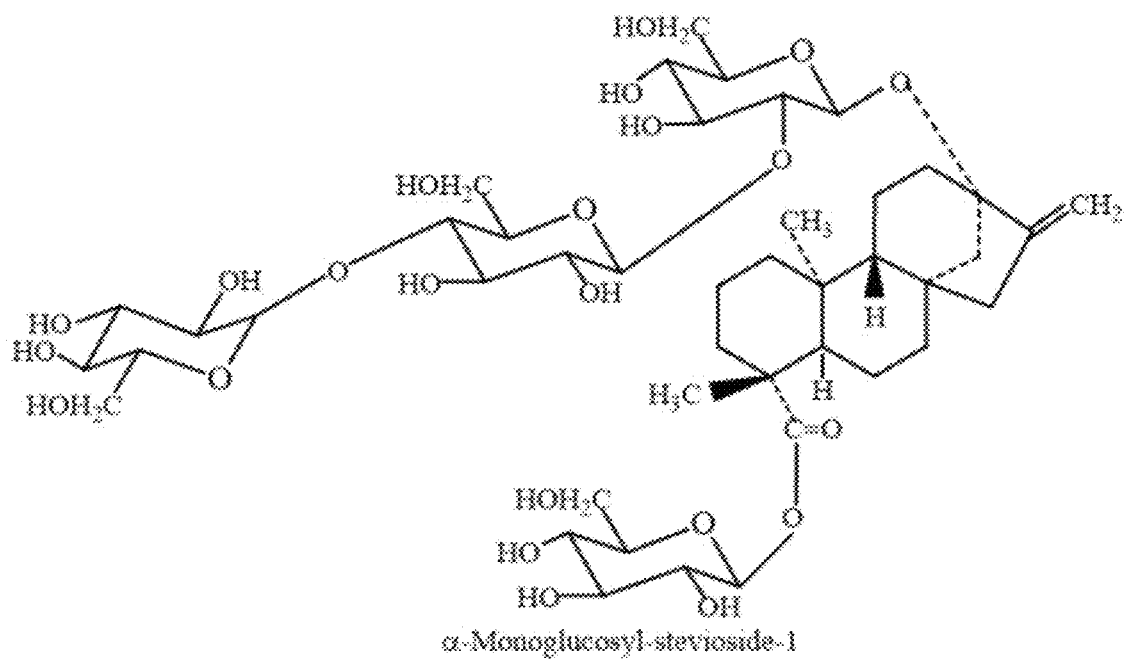
α-Monoglucosyl-stevioside-1
FIG. 3 (cont' d)

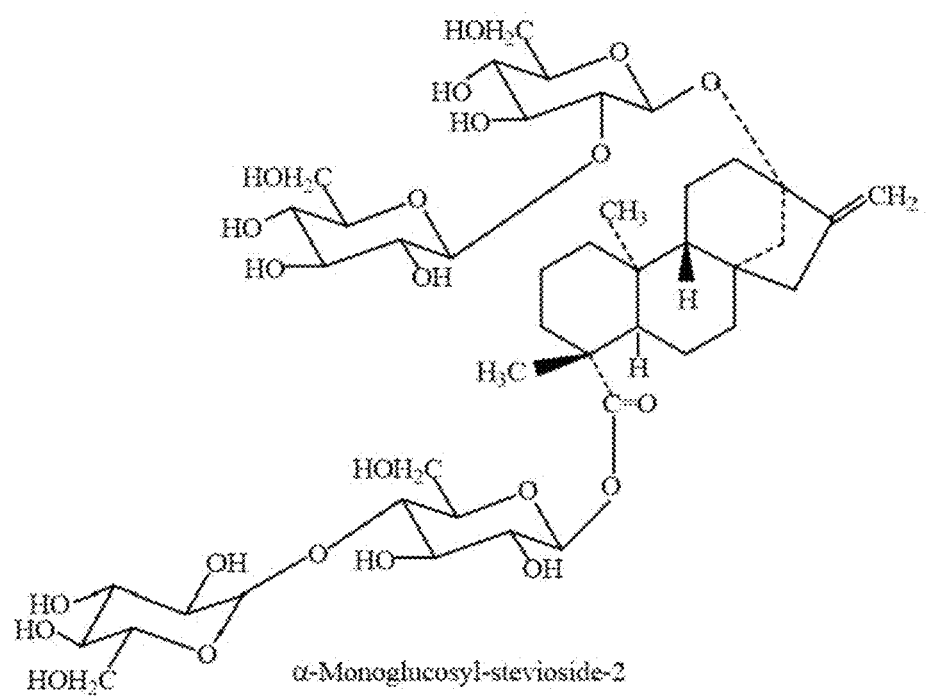
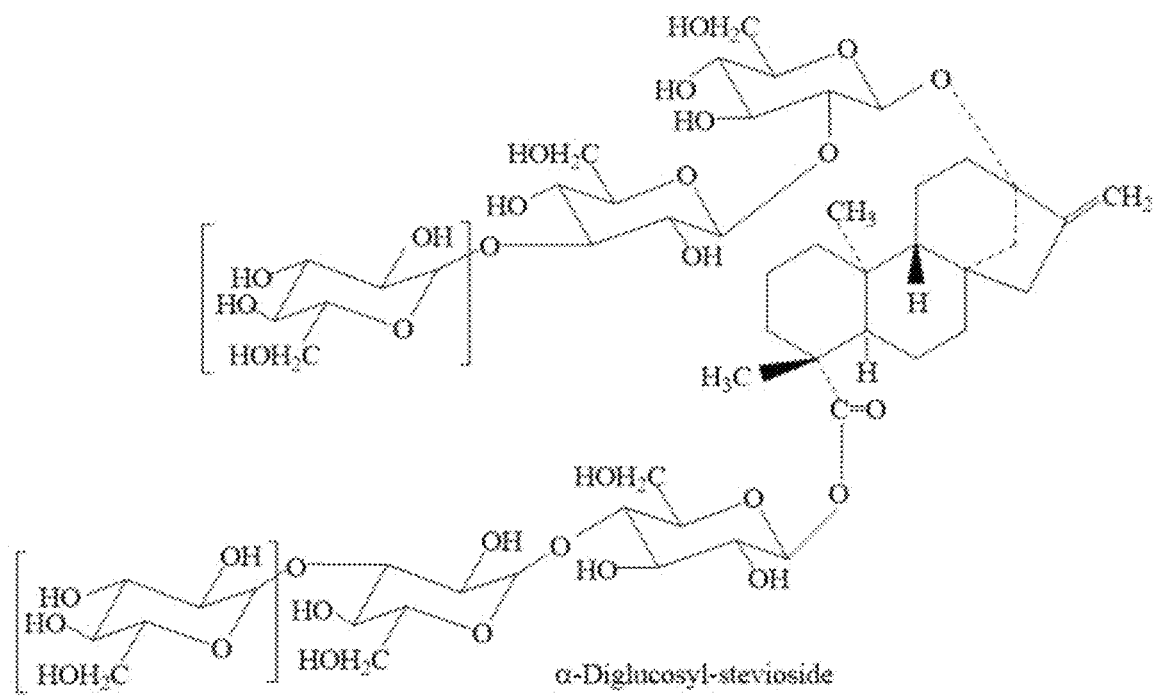
FIG. 3 (cont' d)

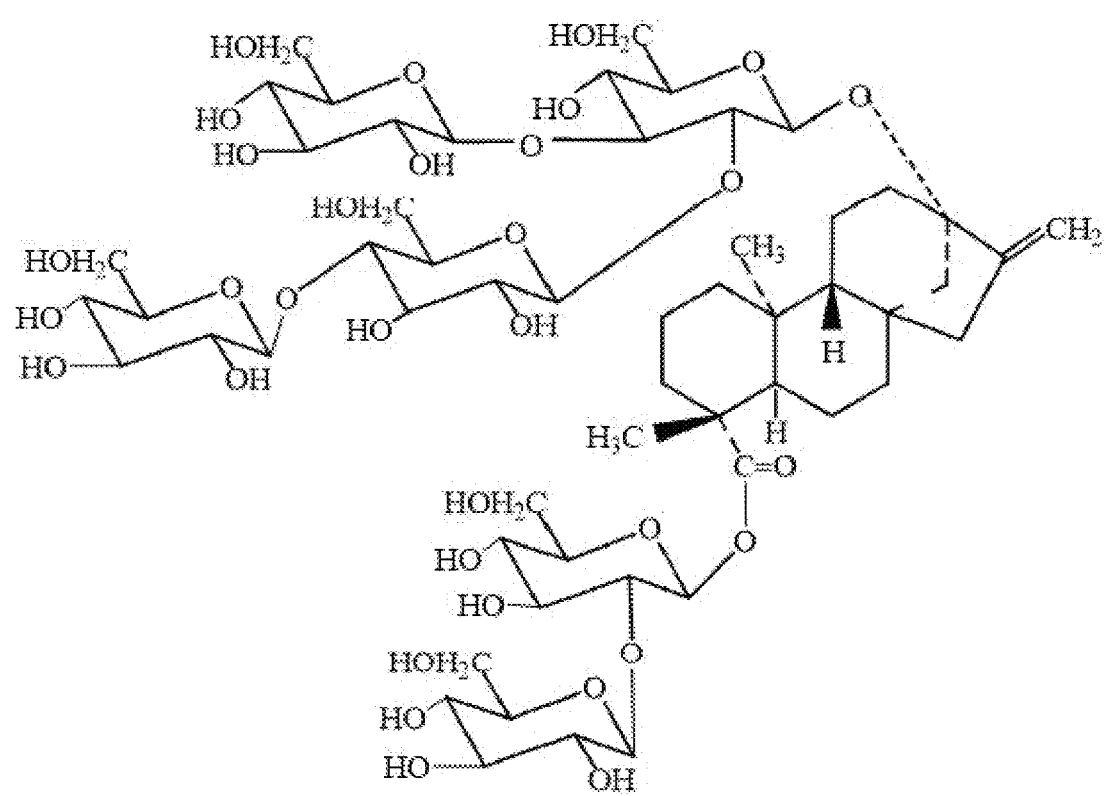
β-1,4-monoglucosylated RebD (B)
FIG. 4 (cont' d)

PROCESSES FOR TRANSGLUCOSYLATION OF STEVIOL GLYCOSIDES

CROSS REFERENCE TO RELATED APPLICATIONS

This application is a national application of PCT/CN2019072212, filed on Jan. 17, 2019. The contents of PCT/CN2019072212 are all hereby incorporated by reference.

TECHNICAL FIELD

The present application relates to the manufacture of steviol glycosides compositions for the field of natural sweeteners and more particularly to processes for transglycosylation of steviol glycosides and the steviol glycosides compositions prepared by the processes, and further to their use in various foods and beverages, cosmetic and pharmaceutical products as a low-calorie sweeteners and flavor modifiers.

BACKGROUND

Intense sweeteners possess sweetness level many times exceeding that of sucrose. They are essentially non-caloric and being used widely in manufacturing of reduced-calorie and diabetic foods. Some of them also possess flavor modifying properties in various systems.

Sweeteners are by no means the simple replicas of sugar. They fail to reproduce the wide range of the functional properties of sugar used by food manufacturers to manipulate color, aroma, texture and shelf-life of their products; which restricts their use in many products. Some sweeteners affect taste adversely, while others are unstable when stored or cooked; some have failed safety trials for human consumption. However, sweeteners may have some cost and functional advantages compared to sugar. The competition among various sugar and non-sugar sweeteners is tough in soft drinks industry, in countries where their use and production are permitted and also in countries with overvalued sugar prices.

At present about twelve intense sweeteners are used worldwide. These are acesulfame-K, alitame, aspartame, cyclamate, glycyrrhizin, neohesperidin dihydrochalcone (Neo-DHC), saccharin, sucralose, thaumatin, neotame, mogrosides, and various steviol glycosides such as stevioside, Rebaudioside A (RebA) and the mixture of them.

The sweeteners can be grouped into a few generations. The first generation represented by cyclamate, glycyrrhizin and saccharin has a long history of use in food. The second generation includes acesulfame-K, aspartame, Neo-DHC and thaumatin. Alitame, neotame, sucralose, stevioside, and RebA belong to the third generation.

The intense sweeteners are used worldwide. The mostly used are aspartame, cyclamate and saccharine. Those, of minor use are acesulfame-K, glycyrrhizin and steviosides. Only a very small consumption is known for alitame, NHDC, and thaumatine.

On the other hand, 'natural' and 'organic' foods and beverages have become the "hottest area" in the food industry. The combination of consumers' desire, advances in food technology, new studies linking diet to disease and disease prevention have created an unprecedented opportunity to address public health through diet and lifestyle.

A growing number of consumers perceive the ability to control their health by improving their present health and/or hedging against future diseases. This creates a demand for food products with enhanced characteristics and associated health benefits, specifically a food and consumer market trend towards "whole health solutions" lifestyle. The term "natural" is highly emotive in the world of sweeteners and has been identified as one of key trust, along with "whole grains", "heart-healthy" and "low-sodium". 'Natural' term is closely related to 'healthier'.

In this respect the sweeteners derived from *Stevia rebaudiana* have undoubted commercial value.

*S. rebaudiana* is a perennial shrub of the Asteraceae (Compositae) family native to certain regions of South America (Paraguay and Brazil). The leaves have been traditionally used for hundreds of years in Paraguay and Brazil to sweeten local teas and medicines.

*Stevia* accumulates the mixture of sweet diterpene glycosides with a single base—steviol but differ by carbohydrate residues at C13 and C19 positions in an amount of approximately 5%-20% of the total dry weight and around 30-450 times sweeter than sugar. Typically, the four major glycosides found in the leaves of *Stevia* are Dulcoside A (DulA), Rebaudioside C (RebC), Rebaudioside A (RebA) and Stevioside. Other glycosides identified in *Stevia* extract include RebB, D, E, F, G, I, H, L, K, J, M, N, and RebO, steviolbioside, and rubusoside (FIG. 1).

Other than being zero-calorie sweeteners, steviol glycosides exhibit diverse kind of pharmacological activities, such as anti-hyperglycemic, anti-hypertensive, anti-inflammatory, anti-tumor, anti-diarrheal, diuretic, and immunomodulatory activities, increase insulin sensitivity and have beneficial effect on blood glucose and insulin levels, i.e. they may have a role in food intake regulation. High purity *Stevia* extracts are approved for use as a sweetener worldwide.

Methods for the recovery of diterpene glycosides from the *Stevia rebaudiana* plant using water or large amounts of organic solvents, such as methanol and ethanol are described in U.S. Pat. Nos. 4,361,697, 4,082,858, 4,892,938, 5,972,120, and U.S. Pat. No. 5,962,678.

Individual glycosides can be purified from *Stevia* biomass extract or synthetized by various methodology described in U.S. patents, for example, U.S. Pat. Nos. 4,353,889; 4,381,402; 4,454,290; 7,838,044; 7,807,206; 7,862,845; U.S. Pat. Appl. 2006/0083838; U.S. Pat. Appl. 2007/0128311; U.S. Pat. Appl. 2008/0300402; U.S. Pat. Appl. 2010/009985; U.S. Pat. Appl. 201110087011; U.S. Pat. Appl. 201110070172.

However, steviol glycosides even in highly purified form possess residual bitterness and aftertaste, which effects on their taste characteristics. Intermolecular transglycosylation with various enzymes results in significant enhancement of their taste profile. The reaction allows adding new carbohydrates at positions C13 and C19. The number of carbohydrate units in the above-mentioned positions determines the quality and degree of component's sweetness as it was shown for stevioside, RebA, and rubusoside using various enzymes as it was described, for example, in U.S. Pat. Nos. 4,219,571; 4,590,160; 7,838,044; 7,807,206; 7,267,835; U.S. Pat. Appl 2003/0236399; U.S. Pat. 2006/013429.

Pullulanase, isomaltase (Lobov S. V., Jasai R., Ohtani K., Tanaka O. Yamasaki K. (1991) Enzymatic production of sweet stevioside derivatives: transglycosylation by glucosidases. Agric. Biol. Chem. 55: 2959-2965), β-galactosidase (Kitahata S., Ishikawa S., Miyata T., Tanaka O. (1989) Production of rubusoside derivatives by transglycosylation of various β-galactosidase. Agric. Biol. Chem. 53: 2923-2928), and dextran saccharase (Yamamoto K., Yoshikawa K., Okada S. (1994) Effective production of glucosyl-stevioside by α-1,6-transglucosylation of dextran dextranase. Biosci. Biotech. Biochem. 58: 1657-1661) have been used as transglycosylating enzymes, together with pullulan, maltose, lactose, and partially hydrolyzed starch, respectively, as donors of glycosidic residues. It is to be noted that each enzyme has its own source of carbohydrate.

The transglucosylation of steviol glycosides was also performed by action of cyclodextrin glucanotransferases (CGTase) produced by various microorganisms, e.g. *Bacillus stearothermophilus* (U.S. Pat. Nos. 4,219,571, and 7,807, 206) as a result α-1,4-glucosyl derivatives were formed with degree of polymerization up to 10.

U.S. Pat. No. 4,219,571 discloses a process for producing a sweetener involving a process which allows glucosyltransferase to react with stevioside in an aqueous solution in order to transform the stevioside into an α-glycosyl-stevioside and hence improve the quality of taste of stevioside by altering the structure of stevioside.

U.S. Pat. No. 8,318,232 discloses a process for simultaneous transglycosylation of the steviol glycosides mixture by acting with a CGTase produced by *Bacillus stearothermophilus* and converting the remaining maltodextrins to fructose-terminated oligosaccharides. In addition, the glucosylated mixture was purified on macroporous resin and deionized to high purity. The products can be used in various applications.

The transglycosylation also successfully carried out using the CGTases produced by *Thermoactinornyces vulgaris* and *Bacillus halophilus* (U.S. Pat. No. 7,838,044).

Rebaudioside C (RebC) is glucosylated by the action of *Bacillus stearothermophilus* CGTase using tapioca starch as a source of glucose unit. The reaction mixture treated with activated carbon, deionized and spray dried. The product contains at least 20% glucosylated RebC, not more than 20% non-modified RebC, and about 20% dextrins (US Pat. Appl 2013/0287894).

Rebaudioside B (RebB) also was glucosylated by the action of *Bacillus stearothermophilus* CGTase using tapioca starch as a source of glucose unit. The reaction mixture treated with activated carbon, and the remaining non-glucosyalted RebB precipitate by adjusting pH and removed by filtration. The filtrate was deionized, purified on macroporous resin and spray dried. The product contains at about 90% of total glycosides with significantly reduced bitterness (US Pat. Appl 2015/0030725).

Similarly, the glucosylation was carried out for Rebaudioside M (RebM) and the product shows improved taste profile (US Pat Appl 2016/0316803).

US Pat Appl 2015/0305380 deals on the glucosylation of rubusoside by treatment of rubusoside and maltodextrin mixture with a CGTase. However, the transglycosylation degree is only in the range of 35-78%. There was some improvement in taste profile.

Transglycosylation reaction significantly accelerates at microwave (Cai et al., 2010) and ultrasound conditions (Jaitak et al., 2009; 2010).

Shortening of glucosylated chains may result in the improvement of taste profile. It can be realized by treatment of transglucosylated products by β-amylase, α-amylase and glucoamylase. The main components of the chromatographically purified mixture are mono- and di-glycosylated glycosides (Kasai et al., 1981; Tanaka, 1987; Miyata et al., 1991a; 1991b; Kitahata, 2001; Toyo Sugar Refining, 2011; US Pat Appl 2012/0214751; US Pat Appl 2017/0303572; US Pat Appl 2017/0208847; U.S. Pat. No. 8,257,948).

The taste profile and sweetness power of glucosyl derivatives are largely dependent on number of additional glucosyl derivatives, i.e. the degree of polymerization of the α-1,4-glucosyl chain. The increase in number of α-1,4-glucosyl residues improved the taste quality but at the same time reduced the sweetness level (Tanaka, 1997).

Regarding to taste profile the best results are obtained when building-up the glucoside chain at position C13 to four units, with position C19 being unchanged. Addition of glucosyl unit to the position C19 results in deterioration of the taste quality. The mono and di-glucosylated derivatives are excellent sugar substitutes and possess best taste qualities among both the intact glycosides and its derivatives (Fukunaga et al., 1989).

Many glucosyl *Stevia* products contain up to 20% residual dextrins and impurities, such as various polyphenolic, flavonoid compounds and their glycosyl derivatives, etc. These admixtures do not possess significant functional properties, reduce the content of steviol glycosides in the product, and some of them affect the taste profile of final preparation.

High content of non-modified glycosides resulting in higher sweetness potency and, at the same time, in deterioration of taste profile.

The sweetness level of the products obtained ranges between 50-120, but the final products contains about 20% of maltooligosaccharides.

In addition, in the glucosylated steviol glycosides from batch-to-batch without proper after-treatment and purification difficult to maintain the ratio of derivatives and non-modified glycosides in the narrow limits. Thus, it is resulting in non-consistence sweetness power, sweetness profile and flavor modifying ability.

On the other hand, reaction conditions can be varied to considerably increase the transglycosylation degree, which is resulting in less amount of non-modified glycosides. It may increase the selectivity of glycosylation and the yield of the final product with shorter reaction time. In addition, it can maximize the economic contribution of the industrial process.

Accordingly, the highly purified glucosylated steviol glycosides with controlled selectivity of glycosylation, low contents of non-modified glycosides and carbohydrate part and consistence ratio of compounds may satisfy the continuous needs of reduced-, low-, and/or non-caloric sweeteners, and flavor modifiers on the base of steviol glycosides with reduced or/no bitterness, without undesirable flavor notes, and sweetness profiles close to natural caloric sweeteners, or combinations of such properties.

SUMMARY

The present application provides compositions comprising α-1,4-glucosylated steviol glycosides resulting from controlled selective glucosylation, where the compositions contain low contents of non-modified glycosides and residual carbohydrate. The compositions have improved characteristics that are suitable for use in various foods and beverages, cosmetic and pharmaceutical products as a low-calorie sweeteners and flavor modifiers.

The compositions of the present application can further comprise other ingredients, such as one or more bulking agents, flavorings, other high intensity and/or reduced calorie and/or caloric sweeteners, vitamins, amino acids and other taste modulators. The present application also relates to incorporation of the compositions into foods and beverages cosmetic and pharmaceutical products.

One aspect of the present application provides a process for producing α-1,4-glucosylated steviol glycosides. In one embodiment, the process comprises:

providing a steviol glycoside and a donor of glucosyl residues, wherein both are mixed in a predetermined ratio to obtain a reaction solution;

adding CGTase for transglucosylation of steviol glycosides to the reaction solution; whereby the reaction solution is incubated at a predetermined temperature for a predetermined period;

passing the reaction solution through a chromatographic column packed with sufficient amount of specific polar macroporous polymeric adsorbent;

washing the column to remove impurities; and eluting adsorbed non-modified steviol glycosides and glycosylated steviol glycosides with an organic solvent solution; and removing the organic solvent, concentrating, and drying to produce a purified sweetener composition comprising α-1,4-glucosylated steviol glycosides.

In another embodiment of the process, the steviol glycosides is represented by the following formula I:

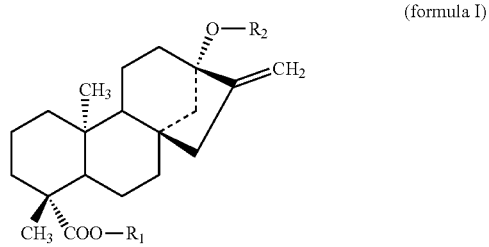

(formula I)

wherein the compound name and corresponding $R_1$ and $R_2$ structures are listed hereinbelow:

| Compound name | R1 (C-19) | R2 (C-13) |
|---|---|---|
| 1. Steviol | H | H |
| 2. Steviolmonoside | H | β-Glc |
| 3. Rubusoside | β-Glc | β-Glc |
| 4. Steviolbioside | H | β-Glc-β-Glc(2→1) |
| 5. Stevioside | β-Glc | β-Glc-β-Glc(2→1) |
| 6. Rebaudioside A | β-Glc | β-Glc-β-Glc(2→1)<br>\|<br>β-Glc(3→1) |
| 7. Rebaudioside B | H | β-Glc-β-Glc(2→1)<br>\|<br>β-Glc(3→1) |
| 8. Rebaudioside C | β-Glc | β-Glc-α-Rha(2→1)<br>\|<br>β-Glc(3→1) |
| 9. Rebaudioside D | β-Glc-β-Glc(2→1) | β-Glc-β-Glc(2→1)<br>\|<br>β-Glc(3→1) |
| 10. Rebaudioside E | β-Glc-β-Glc(2→1) | β-Glc-β-Glc(2→1) |
| 11. Rebaudioside F | β-Glc | β-Glc-β-Xyl(2→1)<br>\|<br>β-Glc(3→1) |
| 12. Dulcoside A | β-Glc | β-Glc-α-Rha(2→1) |
| 13. Dulcoside B | H | β-Glc-α-Rha(2→1)<br>\|<br>β-Glc(3→1) |
| 14. Rebaudioside G | β-Glc | β-Glc-β-Glc(3→1) |
| 15. Rebaudioside I | β-Glc-β-Glc(3→1) | β-Glc-β-Glc(2→1)<br>\|<br>β-Glc(3→1) |
| 16. Rebaudioside H | β-Glc | β-Glc-α-Rha(2→1)-β-Glc(3→1)<br>\|<br>β-Glc(3→1) |
| 17. Rebaudioside L | β-Glc | β-Glc-β-Glc(2→1)<br>\|<br>β-Glc(3→1) } β-Glc(6→1) |
| 18. Rebaudioside K | β-Glc-β-Glc(2→1) | β-Glc-α-Rha(2→1)<br>\|<br>β-Glc(3→1) |

-continued

| Compound name | R1 (C-19) | R2 (C-13) |
|---|---|---|
| 19. Rebaudioside J | β-Glc-α-Rha(2→1) | β-Glc-β-Glc(2→1)<br>|<br>β-Glc(3→1) |
| 20. Rebaudioside M | β-Glc-β-Glc(2→1)<br>|<br>β-Glc(3→1) | β-Glc-β-Glc(2→1)<br>|<br>β-Glc(3→1) |
| 21. Rebaudioside N | β-Glc-α-Rha(2→1)<br>|<br>β-Glc(3→1) | β-Glc-β-Glc(2→1)<br>|<br>β-Glc(3→1) |
| 22. Rebaudioside O | β-Glc-α-Rha(2→1)-<br>β-Glc(3→1) | β-Glc-β-Glc(2→1)<br>|<br>β-Glc(3→1) |

In another embodiment of the process, the steviol glycoside is selected from the group consisting of stevioside, Rebaudioside A (RebA), Rebaudioside B (RebB), Rebaudioside C (RebC), Rebaudioside D (RebD), Rebaudioside E (RebE), Rebaudioside F (RebF), Rebaudioside M (RebM), dulcoside A, steviolbioside, and rubusoside.

In another embodiment of the process, the donor of glucosyl residues is partially hydrolyzed starch, maltooligosaccharides, or a mixture of partially hydrolyzed starch and maltooligosaccharides.

In another embodiment of the process, the partially hydrolyzed starch is prepared by:
  suspending predetermined quantity of starch in distilled or deionized water to obtain a starch suspension; and
  adding CGTase for starch liquefaction to the starch suspension and incubating the suspension at a temperature in a range of 75-80° C. for a period in a range of 0.5-2 hours, preferably 0.8-1.2 hours.

In another embodiment of the process, the starch suspension contains starch in a concentration in a range of 20-40%, preferably 25-33%.

In another embodiment of the process, the CGTase for starch liquefaction is in the range of 1-5 units/gram of starch, preferably 2-3 units.

In another embodiment of the process, the liquefied starch mixture has a dextrose equivalent of 10-25, preferably 12-16.

In another embodiment of the process, the partially hydrolyzing starch further comprises:
  cooling the liquefied starch mixture down to 50-55° C.; and
  adding pullulanase in an amount in the range of 0.3-0.9 units/gram starch, preferably 0.5-0.7 units; whereby the reaction continues for a period of 3-8 hours, preferably 4-6 hours.

In another embodiment of the process, wherein when the partially hydrolyzed starch is used, the starch solution is used without inactivation of CGTase and pullulanase.

In another embodiment of the process, wherein the predetermined ratio of steviol glycosides with the donors of glucosyl residues is in the range of 0.1-1.0 w/w, preferably 0.5-1.0 w/w.

In another embodiment of the process, wherein the CGTase for transglucosylation of steviol glycosides is in an amount in a range of 7-15 units/gram of starch, preferably 8-11 units; the predetermined temperature is in a range of 50-75° C.; and the predetermined period is in a range of 18-72 hours.

In another embodiment of the process, wherein after the reaction with the added CGTase for transglucosylation of steviol glycosides is being carried out for 1-2 hours, a miscible or immiscible organic solvent is added to the reaction mixture in an amount to reach a final concentration in a range of 2-20 v/v %, preferably 7-15%, and the reaction continues for another 18-72 hours at 50-75° C.

In another embodiment of the process, wherein the organic solvent is ethanol, methanol or isopropanol.

In another embodiment of the process, wherein after inactivation of CGTase, the reaction solution is treated with a β-amylase for 5-7 hours at 45-50° C.; wherein the β-amylase is in a range of 5-15 units per gram of total glycosides.

In another embodiment of the process, wherein the polar macroporous polymeric adsorbent is Diaion HP-20, Amberlite XAD-7 and Amberlite XAD-4 or LX-T28.

In another embodiment of the process, wherein the washing includes at least three volumes of RO water, at least two volumes of 0.3-0.5% of NaOH, at least three volumes of RO water, at least two volumes of 8-10% ethanol, at least two volumes of 0.3-0.5% HCl, and then with RO water to pH 5.5-7.0.

In another embodiment of the process, wherein the eluting is with 2-3 volumes of 52-70% ethanol.

Another aspect of the present application provides a steviol glycosides composition, comprising no less than 95% total glycosylated steviol glycosides on an anhydrous basis, wherein the glycosylated steviol glycosides are represented by the following formula II:

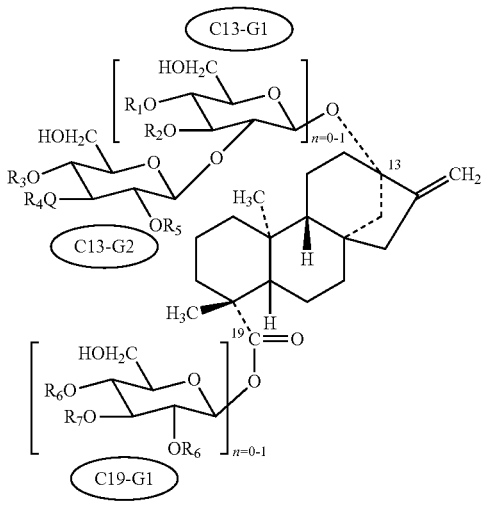

(formula II)

wherein $R_1 = \alpha\text{-}1,4\text{-}(Glu)_{n=0-4}$;
$R_2 = \beta\text{-}1,3\text{-}(Glu)_{n=0-2}$;
$R_3 = \alpha\text{-}1,4\text{-}(Glu)_{n=0-4}$;
$R_5 = \beta\text{-}1,2\text{-}(Glu)_{n=0-2}$;
$R_6 = \alpha\text{-}1,4\text{-}(Glu)_{n=0-4}$;
$R_7 = \beta\text{-}1,3\text{-}(Glu)_{n=0-2}$;
$R_8 = \beta\text{-}1,2\text{-}(Glu \text{ or } Rha)_{n=0-2}$;
wherein C13-G1 is Glu;
C13-G2 is β-Glu; β-Xyl or α-Rha;
C19-G1 is Glu;
wherein Glu is glucose residue;
Xyl is xylose residue;
Rha is Rhamnose residue.

In another embodiment of the steviol glycosides composition, the steviol glycosides composition comprises no less than 95% of total glucosylated steviol glycosides, no more than 5% of residual dextrins, no more than 10% of non-modified steviol glycosides, and no less than 40% of low-degree consisting of mono-, di and tri-glucosylated steviol glycosides.

In another embodiment of the steviol glycosides composition, the steviol glycosides composition comprises no less than 95% of total glucosylated steviol glycosides, no more than 4% of residual dextrins, no more than 8% of non-modified steviol glycosides, and no less than 50% of low-degree consisting of mono-, di and tri-glucosylated steviol glycosides.

In another embodiment of the steviol glycosides composition, the steviol glycosides composition comprises no less than 95% of total glucosylated steviol glycosides, no more than 3% of residual dextrins, no more than 6% of non-modified steviol glycosides, and no less than 60% of low-degree consisting of mono-, di and tri-glucosylated steviol glycosides.

In another embodiment of the steviol glycosides composition, the steviol glycosides composition comprises no less than 95% of total glucosylated steviol glycosides, no more than 3% of residual dextrins, no more than 4% of non-modified steviol glycosides, and no less than 70% of low-degree consisting of mono-, di and tri-glucosylated steviol glycosides.

In another embodiment of the steviol glycosides composition, the steviol glycosides composition comprises no less than 95% of total glucosylated steviol glycosides, no more than 2% of residual dextrins, no more than 2% of non-modified steviol glycosides, and no less than 80% of low-degree consisting of mono-, di and tri-glucosylated steviol glycosides.

In another embodiment of the steviol glycosides composition, the steviol glycosides composition comprises no less than 95% of total glucosylated steviol glycosides, no more than 1% of residual dextrins, no more than 1% of non-modified steviol glycosides, and no less than 85% of low-degree consisting of mono-, di and tri-glucosylated steviol glycosides.

Another aspect of the present application provides a consumable comprising the sweetener composition, wherein the consumable is selected from the group consisting of carbonated soft drinks, ready to drink beverages, energy drinks, isotonic drinks, low-calorie drinks, zero-calorie drinks, sports drinks, cola flavored carbonated soft drinks, fruit flavored carbonated soft drinks, berry flavored carbonated soft drinks, flavored teas, fruit and vegetable juices, juice drinks, dairy drinks, yoghurt drinks, alcohol beverages, powdered beverages, bakery products, cookies, biscuits, baking mixes, cereals, confectioneries, candies, chocolates, toffees, chewing gum, dairy products, flavored milk, yoghurts, flavored yoghurts, cultured milk, soy sauce and other soy base products, salad dressings, mayonnaise, vinegar, frozen-desserts, meat products, fish-meat products, bottled and canned foods, tabletop sweeteners, fruits and vegetables, drug or pharmaceutical preparations, cosmetics, toothpaste, mouthwash, cough syrup, chewable tablets, lozenges, and vitamin preparations.

In another embodiment, the consumable further comprises at least one food ingredient selected from the group consisting of acidulants, organic and amino acids, coloring agents, bulking agents, modified starches, gums, texturizers, preservatives, antioxidants, emulsifiers, stabilizers, thickeners, gelling agents, and a combination thereof.

Another aspect of the present application provides a food, beverage, cosmetic or pharmaceutical product comprising the sweetener composition.

It is understood that both the foregoing general description and the following detailed description are exemplary and explanatory and are intended to provide further explanation of the application as claimed.

BRIEF DESCRIPTION OF THE DRAWINGS

The accompanying drawings are included to provide a further understanding of the application. The drawings illustrate embodiments of the application and together with the description serve to explain the principles of the embodiments of the application.

FIG. 1 shows the structures of known steviol glycosides.

FIG. 2 shows the structures of stevioside, RebA, RebD and RebM, where the shaded rings show the glucose units that are subject to transglycosylation on C4 position ($R_1$-$R_4$).

FIG. 3 shows exemplary structures of alpha-glucosylated derivatives of stevioside and RebA by CGTase.

DETAILED DESCRIPTION

Figure 4:
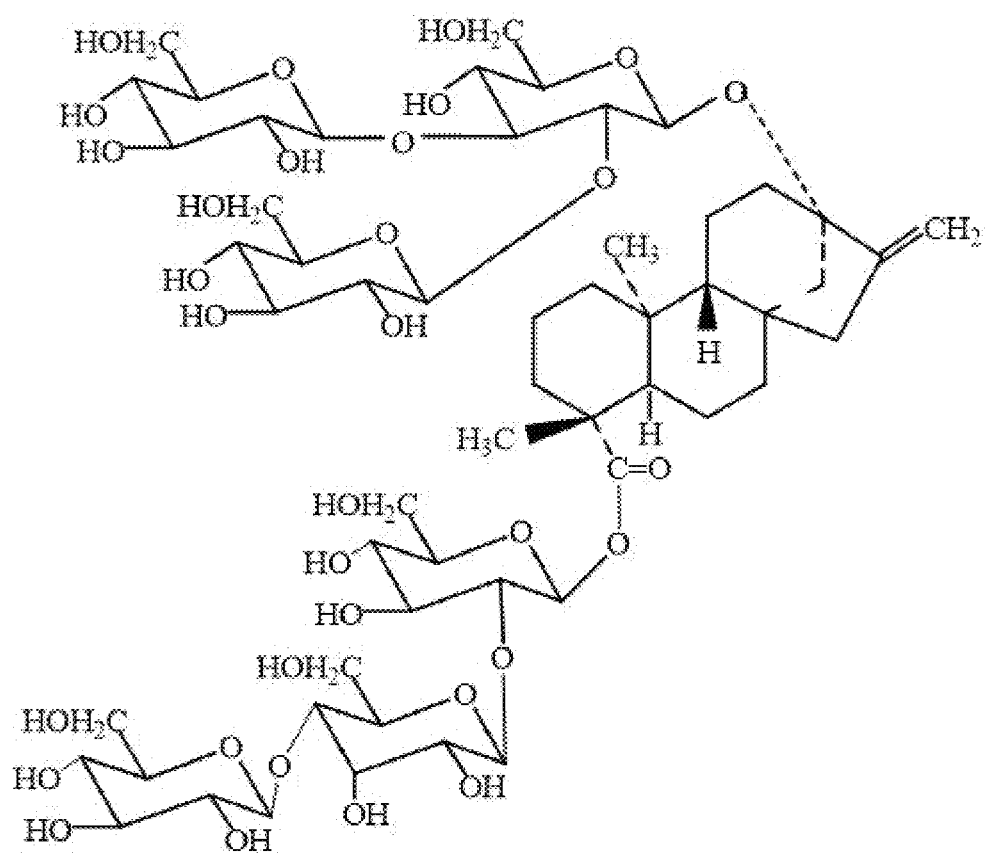
FIG. 4 shows exemplary structures of alpha-glucosylated derivatives of RebD by CGTase.

Advantages of the present application will become more apparent from the detailed description given hereinbelow. However, it should be understood that the detailed description and specific embodiments, while indicating preferred embodiments of the application, are given by way of illustration only, since various changes and modifications within the spirit and scope of the application will become apparent to those skilled in the art from this detailed description.

The present application provides a process for producing α-1,4-glucosylated steviol glycosides, where the process includes the transglucosylation of steviol glycosides and purification of α-1,4-glucosylated steviol glycosides.

In the presence of cyclic or linear maltooligosaccharides or starch, CGTase catalyzes the intermolecular transglycosylation reaction to transfer α-glucosyl units from carbohydrate to C13 and C19 positions of steviol glycosides (α-1,4-transglucosylation).

For the preparation of the sweeteners (i.e. α-1,4-glucosylated steviol glycosides) in the embodiments of the present application, steviol glycosides mixture or individual steviol glycosides of not less than 95% purity commercialized by HB-Natural Ingredients (BENI, Hong Kong) were used. However, the steviol glycosides of various origins produced by precipitation, crystallization or/and chromatographic separation, as well as by microbial, enzymatic and/or chemical synthesis or by combination of them can be used.

The steviol glycosides can be stevioside, Rebaudioside A (RebA), Rebaudioside B (RebB), Rebaudioside C (RebC), Rebaudioside D (RebD), Rebaudioside E (RebE), Rebaudioside F (RebF), Rebaudioside M (RebM), dulcoside A, steviolbioside, rubusoside, as well as other steviol glycosides found in *Stevia rebaudiana Bertoni* plant.

Referring now to FIG. 1, there are provided a summary of the structures of steviol glycosides. FIG. 2 shows the structures of stevioside, RebA, RebD and RebM, where the shaded rings show the glucose units that are subject to transglycosylation on C4 position ($R_1$-$R_4$). As shown in FIG. 1, the basic structure of steviol glycosides is represented by formula I:

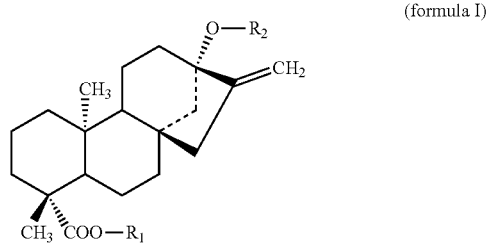

(formula I)

wherein the compound name and corresponding $R_1$ and $R_2$ structures are listed hereinbelow:

| Compound name | R1 (C-19) | R2 (C-13) |
|---|---|---|
| 1. Steviol | H | H |
| 2. Steviolmonoside | H | β-Glc |
| 3. Rubusoside | β-Glc | β-Glc |
| 4. Steviolbioside | H | β-Glc-β-Glc(2→1) |
| 5. Stevioside | β-Glc | β-Glc-β-Glc(2→1) |
| 6. Rebaudioside A | β-Glc | β-Glc-β-Glc(2→1)<br>\|<br>β-Glc(3→1) |
| 7. Rebaudioside B | H | β-Glc-β-Glc(2→1)<br>\|<br>β-Glc(3→1) |
| 8. Rebaudioside C | β-Glc | β-Glc-α-Rha(2→1)<br>\|<br>β-Glc(3→1) |
| 9. Rebaudioside D | β-Glc-β-Glc(2→1) | β-Glc-β-Glc(2→1)<br>\|<br>β-Glc(3→1) |
| 10. Rebaudioside E | β-Glc-β-Glc(2→1) | β-Glc-β-Glc(2→1) |
| 11. Rebaudioside F | β-Glc | β-Glc-β-Xyl(2→1)<br>\|<br>β-Glc(3→1) |
| 12. Dulcoside A | β-Glc | β-Glc-α-Rha(2→1) |
| 13. Dulcoside B | H | β-Glc-α-Rha(2→1)<br>\|<br>β-Glc(3→1) |
| 14. Rebaudioside G | β-Glc | β-Glc-β-Glc(3→1) |
| 15. Rebaudioside I | β-Glc-β-Glc(3→1) | β-Glc-β-Glc(2→1)<br>\|<br>β-Glc(3→1) |

-continued

| Compound name | R1 (C-19) | R2 (C-13) |
|---|---|---|
| 16. Rebaudioside H | β-Glc | β-Glc-α-Rha(2→1)-β-Glc(3→1)<br>\|<br>β-Glc(3→1) |
| 17. Rebaudioside L | β-Glc | β-Glc-β-Glc(2→1)⎤<br>\|                    ⎬ β-Glc(6→1)<br>β-Glc(3→1)    ⎦ |
| 18. Rebaudioside K | β-Glc-β-Glc(2→1) | β-Glc-α-Rha(2→1)<br>\|<br>β-Glc(3→1) |
| 19. Rebaudioside J | β-Glc-α-Rha(2→1) | β-Glc-β-Glc(2→1)<br>\|<br>β-Glc(3→1) |
| 20. Rebaudioside M | β-Glc-β-Glc(2→1)<br>\|<br>β-Glc(3→1) | β-Glc-β-Glc(2→1)<br>\|<br>β-Glc(3→1) |
| 21. Rebaudioside N | β-Glc-α-Rha(2→1)<br>\|<br>β-Glc(3→1) | β-Glc-β-Glc(2→1)<br>\|<br>β-Glc(3→1) |
| 22. Rebaudioside O | β-Glc-α-Rha(2→1)-<br>β-Glc(3→1) | β-Glc-β-Glc(2→1)<br>\|<br>β-Glc(3→1) |

The enzymatic transglucosylation was performed with CGTases produced by Novozymes (Denmark) under brand name Turozyme. However, any type of CGTase in principle can be applied.

The CGTase can be immobilized by any method providing satisfactory activity and stability of the enzyme.

The enzymes can be used as is or after purification.

Starch of various origins, for example, from wheat, corn, potato, tapioca, rice, and sago can be used as donors of glucosyl residues.

Various maltooligosaccharides are also suitable donors of glucosyl residues. Maltooligosaccharides can be linear, branched or cyclic; the exemplary ones include maltodextrins and cyclodextrins.

In some embodiments, the transglycosylation of steviol glycosides comprises providing donors of glucosyl residues and transglucosylating steviol glycosides.

The step of providing the donors of glucosyl residues:

In some embodiments, the donors of glucosyl residues are prepared by liquefying and hydrolyzing starches.

For starch liquefaction, predetermined quantity of starch is suspended in distilled or deionized water, CGTase for starch liquefaction is added to the suspension, and liquefaction of starch is carried out at elevated temperatures 75-80° C. for a period in the range of 0.5-2 hours, preferably 0.8-1.2 hours.

In some embodiments, starch concentration in the starch suspension can be established at around 20-40%, preferably 25-33%.

In some embodiments, the amount of CGTase for starch liquefaction is in the range of 1-5 units/gram of starch, preferably 2-3 units.

In some embodiments, the dextrose equivalent of the liquefied starch mixture can be in the range of 10-25, preferably 12-16.

For hydrolyzing the liquefied starch mixture, the liquefied starch mixture was cooled down to 50-55° C. and a pullulanase is added in an amount in the range of 0.3-0.9 units/gram starch, preferably 0.5-0.7 units and the reaction continues for a period of 3-8 hours, preferably 4-6 hours. In some embodiments, Promozyme-400L (Novozymes) is used. However, any types of pullulanase that is able hydrolyzing alpha-1.6-links in starch can be used. The use of pullulanase in the present application is based on the inventor's discovery that while CGTase cannot break down 1.6-links of starch, the addition of pullulanase increases available quantity of starch and resultant transglucosylation rate and degrees.

In some embodiments, the donors of glucose units are maltooligosaccharides; thus, no need to carry out the liquefaction stage.

In some embodiments, the donors of glucose units are a mixture of partially hydrolyzed starch and maltooligosaccharides.

The step of transglucosylating steviol glycosides:

In some embodiments, steviol glycosides are mixed with the donors of glucosyl residues in an amount in the range of 0.1-1.0 w/w, preferably 0.5-1.0 w/w; the mixture is stirred until a homogeneous solution is obtained. The donors of glucosyl residues can be the partially hydrolyzed starch, maltooligosaccharides, or a mixture of them. In some embodiments, the starch solution is used without inactivation of CGTase and pullulanase.

In some embodiments, CGTase for transglucosylation of steviol glycosides is added to the solution of steviol glycosides and donors of glucosyl residues in an amount in the range of 7-15 units/gram of starch, preferably 8-11 units, and incubated at 50-75° C. for 18-72 hours.

In some embodiments, after the reaction with the added CGTase for transglucosylation of steviol glycosides is being carried out for 1-2 hours, a miscible or immiscible organic solvent, such as ethanol, methanol or isopropanol, etc., is added to the reaction mixture in an amount to reach a final concentration in the range of 2-20 v/v %, preferably 7-15%, and the reaction continues for another 18-72 hours at 50-75° C.

In some embodiments, larger amount of enzyme raises the yield of transglucosylated products and shortens the duration of enzymatic reaction. Also, the higher temperature shortens reaction time. At 55° C. and 60° C., the reaction time is 46-52 hours and 30-32 hours, respectively. At 75° C., the reaction is completed in 12-14 hours.

In some embodiments, at the higher concentrations of raw materials, i.e. low water contents, the degree of transglycosylation is higher and via versa. In any cases, minimizing the water content results in higher degree of transglucosylation.

In some embodiments, the reaction mixture is heated at 90-95° C. for 15-25 min to inactivate the enzymes.

In some embodiments, after inactivation of enzymes including CGTase, the reaction mixture is treated with barley, soybean or microbial β-amylase. The quantity of the enzyme can be around 5-15 units per gram of total glycosides. The reaction time is 5-7 hours at 45-50° C. After reaction is completed, the β-amylase is inactivated by incubating the reaction mixture at a temperature of e.g. 90-95° C. for e.g. 20-30 min.

Some of these data are summarized in the TABLE 1.

52-70% ethanol at BV=1.0-1.5 hour$^{-1}$. Any type of macroporous resins with ability to adsorb the steviol glycoside and their derivatives are suitable for this stage, e.g. Amberlite XAD-7 and Amberlite XAD-4 (commercialized by Rohm & Haas Co., Germany), LX-T28 (Sunresin, China), etc. For desorption of glycosides, methanol or other low chain alcohol can be used instead of ethanol. The combined ethanolic solution of glycosides is treated with 1.0-3.0% of activated carbon from total volume of solution at 20-30° C. for 30-45 min with continuous agitation. After separation of carbon, ethanol is removed by distillation, concentrated using a vacuum evaporation device or nano-filtration and spray dried. Any other appropriate devices can be used for concentration and solidification of the mixture. The product contains more than 95% of total steviol glycosides and 0.5-5% of residual dextrins. The content of non-modified stevioside is around 6-8%. The total amount of low-degree such as mono-, di and tri-glycosylated compounds is in the range of 40-45% (e.g., SAMPLE-1).

In some embodiments, the reaction mixture of transglycosylation of stevioside in the presence of 5-20% of ethanol is treated similarly to the SAMPLE-1. The product contains more than 95% of total steviol glycosides and 0.5-5% of residual dextrins. The content of non-modified stevioside is

TABLE 1

| Reaction mixture | Stevioside DT, % | Stevioside RCT, hrs | RebA DT, % | RebA RCT, hrs | RebD DT, % | RebD RCT, hrs | RebM DT, % | RebM RCT, hrs |
|---|---|---|---|---|---|---|---|---|
| CGT + Starch | 72 | 48 | 70 | 48 | 64 | 60 | 65 | 60 |
| CGT + Pull + Starch + EtOH-0 | 77 | 48 | 74 | 48 | 67 | 60 | 69 | 60 |
| CGT + Pull + Starch + EtOH-5 | 81 | 32 | 79 | 32 | 70 | 40 | 70 | 40 |
| CGT + Pull + Starch + EtOH-10 | 89 | 24 | 86 | 24 | 76 | 30 | 77 | 30 |
| CGT + Pull + Starch + EtOH-15 | 90 | 24 | 88 | 24 | 77 | 30 | 81 | 30 |
| CGT + Pull + Starch + MeOH-10 | 88 | 24 | 84 | 24 | 74 | 40 | 85 | 40 |
| CGT + Pull + Starch + IPA-10 | 89 | 24 | 87 | 24 | 75 | 30 | 75 | 30 |
| CGT + Pull + Starch + γCD + EtOH-0 | 93 | 24 | 91 | 24 | 87 | 24 | 89 | 24 |
| CGT + Pull + Starch + γCD + EtOH-10 | 95 | 18 | 95 | 18 | 92 | 20 | 94 | 20 |

CGT is CGTase. Pull is Pullulanase. EtOH-0, 5, 10, 15 are ethanol concentrations in the reaction mixture: 0%, 5%, 10% and 15%. γCD is gamma-cyclodextrin. DT is Degree of transglycosylation. RCT is Reaction completion time. MeOH is Methanol; IPA is Isopropyl alcohol.

In some embodiments, the purification of the transglucosylated steviol glycosides comprises the following steps.

The step of decolorization: the resulted reaction mixture is treated with 1.0-0.40 w/v % of activated carbon.

The step of purifying of the transglucosylated steviosides from the decolorized reaction mixture:

In some embodiments, for the transglycosylation of stevioside without using an organic solvent during the reaction, the reaction mixture is passed through the chromatographic column packed with sufficient amount of specific polar macroporous polymeric adsorbent, for example Diaion HP-20 (Mitsubishi Chemical Corp, Japan), with bed volume (BV) in the range of 0.2-1.0 hour$^{-1}$ and then the resin is subsequently washed with at least three volumes of reverse osmosis (RO) water, at least two volumes of 0.3-0.5% of NaOH, at least three volumes of RO water, at least two volumes of 8-10% ethanol, at least two volumes of 0.3-0.5% HCl, and then with RO water to pH 5.5-7.0. Desorption of the adsorbed glycosides was carried out with 2-3 volumes of around 3-4%. The total amount of low-degree such as mono-, di and tri-glycosylated compounds is in the range of 45-55% (e,g, SAMPLE-2).

In some embodiments, for the transglycosylation of stevioside without using an organic solvent during the reaction, the reaction mixture is passed through a series of chromatographic columns packed with sufficient amount of specific polar macroporous polymeric adsorbent, e.g. Diaion HP-20 (Mitsubishi Chemical Corp, Japan), with bed volume (BV) around in the range of 0.2-1.0 hour$^{-1}$ and then the resin was washed with 5-6 volumes of RO water. The number of chromatographic columns can be from 4 to 12, preferably from 5 to 8. Then, each column was washed separately with at least two volumes of 0.3-0.5% of NaOH, at least three volumes of RO water, at least two volumes of 8-10% ethanol, at least two volumes of 0.3-0.5% HCl, and then with RO water to pH 5.5-7.0. Desorption of the adsorbed glycosides was carried out with 2-3 volumes of 52-70% ethanol at BV=1.0-1.5 hour$^{-1}$. Any type of macroporous resins with ability to adsorb the steviol glycoside and their derivatives are suitable for this stage, e.g. Amberlite XAD-7 and Amberlite XAD-4 (commercialized by Rohm &z. Haas Co., Germany), LX-T28 (Sunresin, China), etc. For desorption of glycosides, methanol or other low chain alcohol can be used instead of ethanol. The desorption is realized, for each column separately and collected separately. The ethanolic solutions of glycosides is treated with 1.0-3.0% of activated carbon from total volume of solution at 20-30° C. for 30-45 min with continuous agitation. After separation of carbon, ethanol is removed by distillation, concentrated using a vacuum evaporation device or nano-filtration and spray dried. Any other appropriate devices can be used for concentration and solidification of the mixture. The product from the first and last columns containing higher amount of non-modified and deeper glycosylated glycosides, respectively, are recycled to the transglycosylation stage. The products from middle part columns can be mixed or can be used separately. The combined product from middle columns contains more than 95% of total steviol glycosides and 0.2-1.0% of residual dextrins. The content of non-modified stevioside is around 0.5-1.0%. The total amount of low-degree such as mono-, di and tri-glycosylated compounds is in the range of 50-60% (e.g., SAMPLE-3).

In some embodiments, the reaction mixture of transglycosylation of stevioside in the presence of ethanol in the range of 5-20% of is treated similarly to the SAMPLE-3. The combined product from middle columns contains more than 95% of total steviol glycosides and 0.2-1.0% of residual dextrins. The content of non-modified stevioside is around 0.5-1.0%. The total amount of low-degree such as mono-, di and tri-glycosylated compounds is in the range of 55-65% (e.g., SAMPLE-4).

In another embodiment, the transglycosylation of stevioside was carried, out similarly to that of SAMPLE-1 without adding any organic solvent. After inactivation of β-amylase and filtration, the reaction mixture is purified as in the case of SAMPLE-1 The product contains more than 95% of total steviol glycosides and 0.5-5% of residual dextrins. The content of non-modified stevioside is around 10-12%. The total amount of low-degree such as mono-, di and tri-glycosylated compounds is in the range of 55-65% (e.g., SAMPLE-5).

In some embodiments, the reaction mixture of transglycosylation of stevioside in the presence of ethanol in the range of 5-20% is treated similarly to the SAMPLE-5. The product contains more than 95% of total steviol glycosides and 0.5-5% of residual dextrins. The content of non-modified stevioside is around 8-10%. The total amount of low-degree such as mono-, di and tri-glycosylated compounds is in the range of 60-70% (e.g., SAMPLE-6).

In some embodiments, the SAMPLE-6 reaction mixture is purified on the series of columns similarly to SAMPLE-3. The combined product from middle columns contains more than 95% of total steviol glycosides and 0.2-1.0% of residual dextrins. The content of non-modified stevioside is around 0.5-1.0%. The total amount of low-degree such as mono-, di and tri-glycosylated compounds is in the range of 75-85% and more (e.g., SAMPLE-7).

In some embodiments, the transglycosylation of stevioside is realized according to the SAMPLE-7 using beta- and/or gamma-cyclodextrins along with starch as the donors of glucose units (in this case, can we specify the ratio among them or percentage for each component?). The combined product from middle columns contains more than 95% of total steviol glycosides and 0.2-1.0% of residual dextrins. The content of non-modified stevioside is around 0.5-1.0%. The total amount of low-degree such as mono-, di and tri-glycosylated compounds is in the range of 70-88% and more (e.g., SAMPLE-8).

In some embodiments, the transglycosylation is carried out similarly to the SAMPLES-1-8 but using RebA instead of stevioside (e.g., SAMPLE-9-16) (see Table 3).

In some embodiments, the transglycosylation is carried out similarly to the SAMPLES-1-8 but using RebD instead of stevioside (e.g., SAMPLE-17-24) (see Table 4).

In some embodiments, the transglycosylation is carried out similarly to the SAMPLES-1-8 but using RebM instead of stevioside (e.g., SAMPLE-25-32) (see Table 5).

FIG. 3 shows exemplary structures of alpha-glucosylated derivatives of stevioside and RebA by CGTase.

FIG. 4 shows exemplary structures of alpha-glucosylated derivatives of RebD by CGTase.

Figure 5:
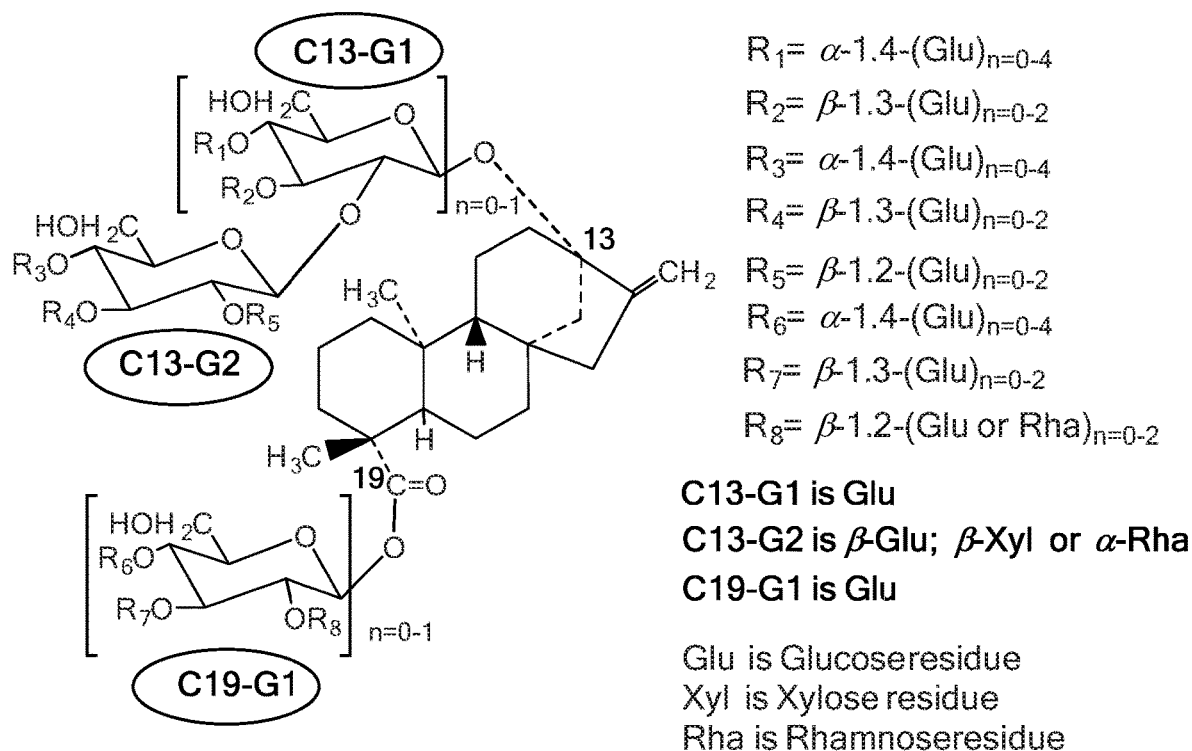
FIG. 5 shows a generalized structure of steviol glycosides and transglycosylated steviol glycosides, where R1, R3 and R6 are the positions that are subject to transglycosylation by CGTase and remaining R locations are naturally or possibly modified positions. The number of transglycosylation points will be correspondingly increased in the case if at R2, R4, R5, R7 and R8 positions there are more glucose, xylose or rhamnose units with free hydroxyl groups at C4.

Referring now to FIG. 5, there is provided a generalized structure of steviol glycosides and transglycosylated steviol glycosides, where R1, R3 and R6 are the positions that are subject to transglycosylation by CGTase, and the remaining R locations are naturally or possibly modified positions. The number of transglycosylation points will be correspondingly increased in the case if at R2, R4, R5, R7 and R8 positions there are more glucose, xylose or rhamnose units with free hydroxyl groups at C4. As shown in FIG. 5, the structure of glycosylated steviol glycosides is represented by formula II:

(formula II)

wherein $R_1 = \alpha\text{-}1,4\text{-}(Glu)_{n=0-4}$;
$R_2 = \beta\text{-}1,3\text{-}(Glu)_{n=0-2}$;
$R_3 = \alpha\text{-}1,4\text{-}(Glu)_{n=0-4}$;
$R_4 = \beta\text{-}1,3\text{-}(Glu)_{n=0-2}$;
$R_5 = \beta\text{-}1,2\text{-}(Glu)_{n=0-2}$;
$R_6 = \alpha\text{-}1,4\text{-}(Glu)_{n=0-4}$;
$R_7 = \beta\text{-}1,3\text{-}(Glu)_{n=0-2}$;
$R_8 = \beta\text{-}1,2\text{-}(Glu \text{ or } Rha)_{n=0-2}$;
wherein C13-G1 is Glu;
C13-G2 is β-Glu; β-Xyl or α-Rha;
C19-G1 is Glu;
wherein Glu is glucose residue;
Xyl is xylose residue;
Rha is Rhamnose residue.

The present application also provides a sweetener composition prepared by the process of the present application.

The sweetener composition comprises residual dextrins, non-modified stevioside, and various degree glucosylated steviol glycosides.

In some embodiments, the sweetener composition comprises no less than 95% of total glucosylated steviol glycosides, no more than 5% of residual dextrins, no more than 10% of non-modified steviol glycosides, and no less than 40% of low-degree glucosylated steviol glycosides consisting of mono-, di and tri-glucosylated steviol glycosides.

In some embodiments, the sweetener composition comprises no less than 95% of total glucosylated steviol glycosides, no more than 4% of residual dextrins, no more than 8% of non-modified steviol glycosides, and no less than 50% of low-degree glucosylated steviol glycosides consisting of mono-, di and tri-glucosylated steviol glycosides.

In some embodiments, the sweetener composition comprises no less than 95% of total glucosylated steviol glycosides, no more than 3% of residual dextrins, no more than 6% of non-modified steviol glycosides, and no less than 60% of low-degree glucosylated steviol glycosides consisting of mono-, di and tri-glucosylated steviol glycosides.

In some embodiments, the sweetener composition comprises no less than 95% of total glucosylated steviol glycosides, no more than 3% of residual dextrins, no more than 4% of non-modified steviol glycosides, and no less than 70% of low-degree glucosylated steviol glycosides consisting of mono-, di and tri-glucosylated steviol glycosides.

In some embodiments, the sweetener composition comprises no less than 95% of total glucosylated steviol glycosides, no more than 2% of residual dextrins, no more than 2% of non-modified steviol glycosides, and no less than 80% of low-degree glucosylated steviol glycosides consisting of mono-, di and tri-glucosylated steviol glycosides.

In some embodiments, the sweetener composition comprises no less than 95% of total glucosylated steviol glycosides, no more than 1% of residual dextrins, no more than 1% of non-modified steviol glycosides, and no less than 85% of low-degree consisting of mono-, di and tri-glucosylated steviol glycosides.

For RebD and RebM, they do not dissolve completely without maltooligosaccharides and the precipitates are separated by filtration. maltooligosaccharides can be used in an amount of 1:1, mol/mol to the glycoside.

The separation of steviol glycosides glycosylated derivatives can be realized by any suitable way such as liquid chromatography on silica gel or preparative HPLC on 3-aminopropyl-functionalized silica gel or other appropriate carrier using an appropriate mobile phase, for example, linear gradient of acetonitrile and water as it was described previously (Starratt A. N., Kirby C. W., Pocs R., Brandle J. E. (2002) Rebaudioside F, a diterpene glycoside from *Stevia rebaudiana. Phytochemistry.* 59. 367-370; Kohda H, Kasi R, Yamasaki K, Murakami K, Tanaka O (1976) New sweet diterpene glucoside from *Stevia rebaudiana. Phytochemistry* (Oxford). 15. 981-983; Chaturvedula V. S. P., Upreti M. and I. Prakash (2011) Structures of the novel α-glucosyl linked diterpene glycosides from *Stevia rebaudiana. Carb. Res.* 346 (13). 2034-2038) and others.

Furthermore, the inventor of the present application discovered that the efficient transglycosylation of RebD, RebM and RebB is possible only in the presence of maltooligosaccharides because of solubility.

Because of steric hindrance only three glucose residues of RebD, namely 13-G1, 13-G2 and 19-G2 are liable to α-1,4-transglucosylation under the action of CGTase. In the case of RebM the glucose units 13-G1, 13-G2, 19-G1 and 19-G2 are more subject to transglycosylation that 13-G3 and 19-G3. In RebA the glucosylation primary can happen at 13-G1, 13-G2 and 19-G1. All the glucose units of stevioside can undergo to transglycosylation at the almost same rate (FIG. 2).

The efficiency of transglycosylation is higher in the case of using starch as the source of glucosyl units; however, the content of most desirable in terms of taste profile mono- and di-glucosylated derivatives is higher in the case of maltooligosaccharides. In the presence of an organic solvents and higher reaction mixture concentrations the reaction time is shorter and degree of transglycosylation is higher. As a first application in transglycosylation of steviol glycosides, addition of pullulanase increases the degree of transglycosylation for about 5-7%.

The activity of CGTases according to the present application is determined by the following assay. The mixture of 10 μL enzyme and 0.2% amylose solution in 0.2M buffer was incubated at 50° C. for 10 min. The reaction was stopped by adding 1 mL 0.5M acetic acid and 0.5 mL 0.02% $I_2$/0.2% KI solution. The mixture volume was brought up to 10 mL with distilled water, and extinction was determined under 700 nm. The enzyme activity unit was accepted as the enzyme quantity that has reduced the intensity of blue color by 10% for 1 min.

β-Amylase activity unit (1 AUN) is defined as the activity which liberates 100 μg of reducing sugar (expressed by dextrose equivalent) per minute under the following conditions: 1 mL of enzyme solution is mixed with 5 mL of 1.2% starch solution (pH 5.5, M/20 acetate buffer) and kept for 20 min at 40° C.

HPLC analysis of non-modified steviol glycosides was realized on Agilent 1100 series (USA) chromatograph. Separation of steviol glycosides was performed on Zorbax $NH_2$ (150×4.6 mm; 5 μm) chromatographic column. The flow rate was 1.0 mL/min and the mobile phase was 80:20 (v/v) acetonitrile and water (containing 0.025% acetic acid) mixture. For the identification a LTV detector at 2010 nm was used. The reference materials for steviol glycosides quantitation were standards from Chromadex Inc. (USA). The steviol glycosides were identified by their retention times, the concentrations calculated by an external standards method and reported on a dry weight basis.

In some embodiments the identification of non-modified glycosides was carried out by HPLC using an Agilent Technologies 1100 Series (USA) equipped with a Ameritech Luna C-18 (250×4.6 mm; 5 μm) chromatographic column using the gradient of 0.01 mol/L phosphate buffer (pH 2.6) and an acetonitrile/0.01 mol/L phosphate buffer (pH 2.6) mixture (50:50, v/v) from 60:40 (v/v) to 40:60 (v/v) during 60 minutes at 40° C. and LW detector at 210 nm.

HPLC analysis of the transglycosyalted product was realized using an Agilent Technologies 1100 Series (USA) equipped with a Zorbax $NH_2$ (150×4.6 mm; 5 μm) column using an acetonitrile-water gradient from 80:20 (v/v) (2 minutes) to 50:50 (v/v), for 70 minutes and UV detector at 210 nm.

Determination of total steviol glycosides and total content of glycosylated derivatives were realized by adsorption/desorption on macroporous resin Diaion HP-20.

The sensory assessment of samples was carried using aqueous solutions, with 22 panelists. Using the results of preliminary test on the sweetening power of the sweeteners, the aqueous solutions were prepared that exhibited a sweetness comparable to that of 5% aqueous sucrose solution. The most desirable and most undesirable samples were chosen based on overall acceptance (TABLE 2-TABLE 5).

TABLE 2

Assessment of glycosylated stevioside

| Item | S1 | S2 | S3 | S4 | S5 | S6 | S7 | S8 |
|---|---|---|---|---|---|---|---|---|
| Non-modified | 7.2 | 3.7 | 0.9 | 0.7 | 11.2 | 10.8 | 0.6 | 0.5 |
| T-M-D-Tri | 44 | 52 | 77 | 82 | 62.5 | 64.5 | 85 | 86 |
| DT, % | 78 | 89 | 95 | 96 | 82 | 83 | 97 | 97 |
| SE | 160 | 140 | 130 | 130 | 170 | 170 | 120 | 120 |
| RD, % | 3.4 | 3.1 | 0.5 | 0.7 | 4.1 | 3.8 | 0.5 | 0.5 |
| Most desirable | 0 | 2 | 4 | 4 | 0 | 0 | 5 | 7 |
| Most undesirable | 3 | 2 | 1 | 1 | 7 | 6 | 0 | 0 |
| Organoleptic | Sweet, light, soft, round, pleasant, close to sucrose, no lingering aftertaste, onset is rapid. | | | | Sweet, slightly bitter, astringent, no lingering aftertaste | | Sweet, light, soft, round, pleasant, close to sucrose, no lingering after-taste, onset is rapid. | |

S1-S8 are the samples. SE is the degree of sweetness compared to 5% sucrose in water. T-M-D-Tri is total amount of Mono-Glu, Di-Glu, Tri-Glu derivatives of stevioside. RD is residual dextrin. DT is degree of transglycosylation.
Note:
In the presence of 10% ethanol the reaction can be completed in 18-24 hrs.

TABLE 3

Assessment of glycosylated RebA

| Item | S9 | S10 | S11 | S12 | S13 | S14 | S15 | S16 |
|---|---|---|---|---|---|---|---|---|
| Non-modified | 7.5 | 4.5 | 1.0 | 0.9 | 11.5 | 11.2 | 0.7 | 0.5 |
| T-M-D-Tri | 46.4 | 53 | 79 | 86 | 64.3 | 64.6 | 85 | 87 |
| DT, % | 76.7 | 85 | 95 | 96 | 83 | 83 | 97 | 97 |
| SE | 170 | 150 | 140 | 140 | 170 | 170 | 130 | 130 |
| RD, % | 3.2 | 3.1 | 0.6 | 0.7 | 4.5 | 3.6 | 0.6 | 0.7 |
| Most desirable | 0 | 2 | 3 | 3 | 0 | 0 | 6 | 8 |
| Most undesirable | 3 | 2 | 1 | 1 | 7 | 6 | 0 | 0 |
| Organoleptic | Sweet, light, soft, round, pleasant, close to sucrose, no lingering bitter aftertaste, onset is rapid. | | | | Sweet, slightly bitter, no lingering bitter aftertaste | | Sweet, light, soft, round, pleasant, close to sucrose, no lingering bitter aftertaste, onset is rapid. | |

S9-S16 are the samples. SE is the degree of sweetness compared to 5% sucrose in water. T-M-D-Tri is total amount of Mono-Glu, Di-Glu, Tri-Glu derivatives of stevioside. RD is residual dextrin. DT is degree of transglycosylation.
Note:
In the presence of 10% ethanol the reaction can be completed in 18-24 hrs.

TABLE 4

Assessment of glycosylated RebD

| Item | S17 | S18 | S19 | S20 | S21 | S22 | S23 | S24 |
|---|---|---|---|---|---|---|---|---|
| Non-modified | 11.2 | 9.4 | 3.1 | 0.7 | 16.4 | 19.6 | 0.7 | 0.6 |
| T-M-D-Tri | 42.3 | 47 | 78 | 88 | 61.2 | 62.5 | 88 | 87 |
| DT, % | 72.2 | 76 | 94 | 95 | 81 | 84 | 95 | 97 |
| SE | 160 | 150 | 140 | 140 | 170 | 170 | 130 | 130 |
| RD, % | 3.3 | 3.2 | 0.8 | 0.7 | 3.1 | 3.2 | 0.6 | 0.7 |
| Most desirable | 0 | 3 | 3 | 4 | 0 | 0 | 5 | 7 |
| Most undesirable | 3 | 2 | 1 | 1 | 7 | 6 | 0 | 0 |
| Organoleptic | Sweet, light, soft, round, pleasant, close to sucrose, no lingering bitter aftertaste, onset is rapid. | | | | | | | |

S17-S24 are the samples. SE is the degree of sweetness compared to 5% sucrose in water. T-M-D-Tri is total amount of Mono-Glu, Di-Glu, Tri-Glu derivatives of stevioside. RD is residual dextrin. DT is degree of transglycosylation.
Note:
In the presence of 10% ethanol the reaction can be completed in 18-24 hrs.

TABLE 5

Assessment of glycosylated RebM

| Item | S25 | S26 | S27 | S28 | S29 | S30 | S31 | S32 |
|---|---|---|---|---|---|---|---|---|
| Non-modified | 11.5 | 9.1 | 2.8 | 0.6 | 15.5 | 17.8 | 0.6 | 0.6 |
| T-M-D-Tri | 48.6 | 52.4 | 78 | 88 | 61.2 | 62.5 | 88 | 87 |
| DT, % | 77.4 | 79.4 | 95 | 95 | 85 | 88 | 96 | 97 |
| SE | 160 | 150 | 140 | 130 | 170 | 170 | 130 | 130 |
| RD, % | 3.1 | 3.0 | 0.7 | 0.7 | 3.4 | 3.0 | 0.6 | 0.6 |
| Most desirable | 0 | 3 | 3 | 3 | 0 | 0 | 5 | 8 |
| Most undesirable | 3 | 3 | 1 | 0 | 7 | 6 | 0 | 0 |
| Organoleptic | Sweet, light, soft, round, pleasant, close to sucrose, no lingering aftertaste, onset is rapid. | | | | | | | |

S25-S32 are the samples. SE is the degree of sweetness compared to 5% sucrose in water. T-M-D-Tri is total amount of Mono-Glu, Di-Glu, Tri-Glu derivatives of stevioside. RD is residual dextrin. DT is degree of transglycosylation.
Note:
In the presence of 10% ethanol the reaction can be completed in 18-24 hrs.

As apparent from the results in TABLEs 2-5, all the samples produced by above-mentioned methods are possessing high acceptability and excellent taste profile without bitterness. Slight bitterness was mentioned only in the cases of preparations with higher content of non-modified stevioside (Samples 5 and 6) and RebA (Samples 13 and 14) that are produced by treatment with beta-amylase or glucoamylase without separation on the series of columns.

The most desirable samples are the product produced in the presence of 10% ethanol, treated with beta-amylase and separated on the chromatographic columns. It was chosen for all the glycosides subjected to transglycosylation, i.e. stevioside (Samples 7 and 8), RebA (Samples 15 and 16), RebD (Samples 23 and 24), and RebM (Samples 31 and 32). Thus, the sweetness quality of these samples was rated as most superior.

Overall the samples with low-content of non-modified glycosides, i.e. the products prepared by chromatographic separation from middle columns (Samples 3, 4, 11, 12, 19, 20, 27, and 28) possessed better taste profiles compared to samples with remaining non-modified glycosides. However, their sweetening power is inferior.

The most desirable preparations were produced using cyclodextrins. Most probably, in the presence of cyclodextrins, the transglycosylation at C13 is predominant.

In all the cases, the samples prepared in the presence of ethanol possessed better taste profile compared to that produced only in water system because of higher transglycosylation degree.

The products can be standardized either by the content of mono-, di- and/or tri-glycosylated derivatives, total sum of them, by content of total steviol glycosides, non-reacted glycosides or by sweetness level.

The glycosylated derivatives produced according to this application can be used as sweetening or flavor agents alone or in combination with other naturally occurring or artificial high intensity or bulk sweeteners, sweetener suppressors, umami taste enhancers, amino acids and their derivatives, polyols or sugar alcohols, reduced calorie sweeteners, various carbohydrates, various physiologically active substances or functional ingredients, flavoring agents of natural or artificial origins, aroma-forming compounds, organic and inorganic acids and their salts, bitter compounds, taste modifiers, bitter blockers, vitamins, dietary fibers, polyphenols, etc.

The compounds alone or in combination with other substances can be used in various food and beverage products, cosmetics and pharmaceutical compositions.

Non-limiting examples of food and beverage products include carbonated soft drinks, ready to drink beverages, energy drinks, isotonic drinks, low-calorie drinks, zero-calorie drinks, sports drinks, teas, fruit and vegetable juices, juice drinks, dairy drinks, yoghurt drinks, alcohol beverages, powdered beverages, bakery products, cookies, biscuits, baking mixes, cereals, confectioneries, candies, toffees, chewing gum, dairy products, flavored milk, yoghurts, flavored yoghurts, cultured milk, soy sauce and other soy base products, salad dressings, mayonnaise, virtegar, frozen-desserts, meat products, fish-meat products, bottled and canned foods, tabletop sweeteners, fruits and vegetables.

Additionally, the compositions can be used in drug or pharmaceutical preparations and cosmetics, including but not limited to toothpaste, mouthwash, cough syrup, chewable tablets, lozenges, vitamin preparations, and the like.

The compositions can be used "as-is" or in combination with other sweeteners, flavors and food ingredients.

Non-limiting examples of sweeteners include steviol glycosides, stevioside, Rebaudioside A, Rebaudioside B, Rebaudioside C, Rebaudioside D, Rebaudioside E, Rebaudioside F, dulcoside A, steviolbioside, rubusoside, as well as other steviol glycosides found in *Stevia rebaudiana Bertoni* plant and mixtures thereof, stevia extract, Luo Han Guo extract, mogrosides, high-fructose corn syrup, corn syrup, invert sugar, fructooligosaccharides, inulin, inulooligosaccharides, coupling sugar, maltooligosaccharides, maltodextrins, corn syrup solids, glucose, maltose, sucrose, lactose, aspartame, saccharin, sucralose, sugar alcohols.

Non-limiting examples of flavors include lemon, orange, fruity, banana, grape, pear, pineapple, bitter almond, cola, cinnamon, sugar, cotton candy, vanilla flavors.

Non-limiting examples of other food ingredients include flavors, acidulants, organic and amino acids, coloring agents, bulking agents, modified starches, gums, texturizers, preservatives, antioxidants, emulsifiers, stabilizers, thickeners, gelling agents.

The following embodiments illustrate various embodiments of the application. It will be understood that the application is not limited to the materials, proportions, conditions and procedures set forth in the embodiments, which are only illustrative.

Embodiment 1

Preparation of Composition 100 grams of tapioca starch were suspended in 200 mL distilled water (pH 6.5-7.0), 60 units of CGTase produced by Novozymes (Denmark) under brand name Turozyme were added, and the liquefaction of starch was carried out at 75-80° C. for about one hour to dextrose equivalent about 10-20. After cooling to 55° C., pullulanase (Promozyme-400L, Novozymes) was added in an amount 0.5 units/gram starch and the reaction continued for another 5 hours.

One hundred grams of stevioside with 95% of purity commercialized by HBNI (China) were added and mixed until a homogeneous solution was obtained. 300 units of CGTase (Novozymes, Denmark) were added to the solution and the transglycosylation was realized at 65° C. for 24 hours with continuous agitation. The reaction mixture was heated at 95° C. for 15 minutes to inactivate the enzyme, decolorized with 0.5% (w/v) of activated carbon. The filtrate was passed through the chromatographic column (5.0×50 cm) packed with the specific polar macroporous polymeric adsorbent Diaion HP-20 (Mitsubishi Chemical Corporation, Japan) with 0.5 hour$^{-1}$ bed volume (BV) at ambient temperature and then washed with five volumes of RO water, two volumes of 0.5% of NaOH, three volumes of RO water, two volumes of 10% ethanol, two volumes of 0.5% HCl, and then with RO water to pH 5.5-7.0. Desorption of the adsorbed glycosides was carried out with 3 volumes of 52% ethanol at BV=1.0 hour$^{-1}$. The combined ethanolic solution of glycosides was treated with 1.0% activated carbon from total volume of solution at 25° C. for 30 min with continuous agitation. The used carbon was separated by filtration, ethanol was removed by distillation and the resulted refined solution concentrated and dried to produce 152 grams of a sweetener composition with total steviol glycosides content 97.2%, comprising 7.2% of non-modified stevioside, 44% of total mono-, di- and tri-glucosylated derivatives, and 3.4% of carbohydrate part on dry base. The sweetener composition corresponds to SAMPLE-1 that was around 160 sweeter than 5% sucrose solution in water.

Embodiment 2

Preparation of Composition 100 grams of tapioca starch were suspended in 200 mL distilled water (pH 6.5-7.0), 60 units of CGTase produced by Novozymes (Denmark) under brand name Turozyme were added, and the liquefaction of starch was carried out at 75-80° C. for about one hour to dextrose equivalent about 15. After cooling to 55° C., pullulanase (Promozyme-400L, Novozymes) was added in an amount 0.5 units/gram starch and the reaction continued for another 5 hours.

One hundred grams of stevioside with 95% of purity commercialized by HBNI (China) were added and mixed until a homogeneous solution was obtained. 300 units of CGTase (Novozymes, Denmark) were added to the solution and the transglycosylation was realized at 65° C. for 2 hours with continuous agitation. 40 mL of absolute ethanol to 10% final concentration was added to the reaction mixture and the reaction continue to another 22 hours. The further treatment of the reaction mixture was carried out according to the procedure of EMBODIMENT-1. A sweetener composition yield was 158 grams with total steviol glycosides content 97.6%, comprising 3.7% of non-modified stevioside, 52% of total mono-, di- and tri-glucosylated derivatives, and 3.1% of carbohydrate part on dry base. The sweetener composition corresponds to SAMPLE-2 that was around 140 sweeter than 5% sucrose solution in water.

Embodiment 3

Preparation of Composition

The reaction between stevioside and starch was carried out according to the procedure of EMBODIMENT-1. The reaction mixture after inactivation of enzymes and treatment with activated carbon, was passed trough five parallelly connected columns (2×30 cm) containing 20 mL of the specific polar macroporous polymeric adsorbent Diaion HP-20 (Mitsubishi Chemical Corporation, Japan) with 0.5 hour$^{-1}$ BV following by washing with five volumes of RO water. Then, each column was washed separately with two volumes of 0.5% of NaOH, three volumes of RO water, two volumes of 10% ethanol, two volumes of 0.5% HCl, and then with RO water to pH 5.5-7.0. Desorption of the adsorbed glycosides was carried out separately with 3 volumes of 52% ethanol at BV=1.0 hour$^{-1}$.

The product from the first and last columns contained higher amount of non-modified and deeper glycosylated glycosides, respectively. They were recycled to the transglycosylation stage. The products from columns 2-4 were mixed and the combined solution of glycosides treated with 1.0% activated carbon from total volume of solution at 25° C. for 30 min with continuous agitation. The used carbon was separated by filtration, ethanol was removed by distillation and the resulted refined solution concentrated and dried to produce 142 g of sweetener composition corresponded to SAMPLE-3.

It contained 98.4% of total steviol glycosides, comprising 0.9% of non-modified stevioside, 77% of total mono-, di- and tri-glucosylated derivatives, and 0.5% of carbohydrate part on dry base. It was approximately 130 times sweeter than 5% sucrose solution in water.

Embodiment 4

Preparation of Composition

The experiment was carried out according to the procedure of EMBODIMENT-3 but in the presence of 10% of ethanol as it is in the EMBODIMENT-2. The combined product from the columns 2-4 in an amount 148 g, contained 98.6% of total steviol glycosides, comprising 0.7% of non-modified stevioside, 82% of total mono-, di- and tri-glucosylated derivatives, and 0.5% of carbohydrate part on dry base. It was approximately 130 times sweeter than 5% sucrose solution in water. The sweetener composition corresponds to the SAMPLE-4.

Embodiment 5

Preparation of Composition

The transglycosylation of stevioside was carried out according to the procedure of EMBODIMENT-1. After inactivation of enzymes, the reaction mixture temperature was reduced to 50° C. and treated with 2000 units of soybean β-amylase Nokozyme SBA-80 (Noke Biotech., China) for 6 hours. The reaction mixture was heated at 95° C. for 15 minutes to inactivate the β-amylase and purified according to the EMBODIMENT-1. The yield of the sweetener composition was 121 g and corresponded to the SAMPLE-5. It contained 95.5% of total steviol glycosides, comprising 11.2% of non-modified stevioside, 62.5% of total mono-, di- and tri-glucosylated derivatives, and 4.1% of carbohydrate part on dry base. It was approximately 170 times sweeter than 5% sucrose solution in water.

Embodiment 6

Preparation of Composition

The reaction mixture of transglycosylation of stevioside in the presence of 10% of ethanol was treated similarly to the EMBODIMENT-5. The combined product in an amount 126 g, contained 96.4% of total steviol glycosides, comprising 10.8% of non-modified stevioside, 64.5% of total mono-, di- and tri-glucosylated derivatives, and 3.8% of carbohydrate part on dry base. It was approximately 170 times sweeter than 5% sucrose solution in water. The sweetener composition corresponds to the SAMPLE-6.

Embodiment 7

Preparation of Composition

The reaction mixture of the EMBODIMENT-6 was purified on the series of columns similarly to EMBODIMENT-3. The combined product from the columns 2-4 in an amount 115 g, contained 98.8% of total steviol glycosides, comprising 0.6% of non-modified stevioside, 85% of total mono-, di- and tri-glucosylated derivatives, and 0.5% of carbohydrate part on dry base. It was approximately 120 times sweeter than 5% sucrose solution in water. The sweetener composition corresponds to the SAMPLE-7.

Embodiment 8

Preparation of Composition

One hundred sixty grams of γ-cyclodextrin and 100 grams of stevioside (1:1, mol/mol) were suspended in 600 mL distilled water (pH 6.5-7.0) and the mixture was incubated with continuous agitation for 60 min at 60° C. until clear solution is obtained. It was cooled to an ambient temperature and mixed with 100 g of starch. Then, the liquefaction and transglycosylation reaction was carried out according to EMBODIMENT-6 in the presence of 10% ethanol and treatment with β-amylase. The reaction mixture was purified on the series of columns packed with macroporous resin. The combined product from the columns 2-4 in an amount 118 g, contained 98.8% of total steviol glycosides, comprising 0.5% of non-modified stevioside, 86% of total mono-, di- and tri-glucosylated derivatives, and 0.5% of carbohydrate part on dry base. It was approximately 120 times sweeter than 5% sucrose solution in water. The sweetener composition corresponds to the SAMPLE-8.

Application of cyclodextrins as the donors of glucosyl residues resulted in higher content of mono- and di-glucosylated derivatives compared to starch. In addition, with an increase of the amount of cyclodextrin, the concentration of non-reacted glycosides decreased.

Embodiment 9-16

Preparation of Composition

The samples were prepared according to EMBODIMENTS-1-8 using RebA instead of stevioside. The data are summarized in the TABLE-3.

Embodiment 17-24

Preparation of Composition

The samples were prepared according to EMBODIMENTS-1-8 using RebD instead of stevioside. The data are summarized in the TABLE-4.

Embodiment 25-32

Preparation of Composition

The samples were prepared according to EMBODIMENTS-1-8 using RebM instead of stevioside. The data are summarized in the TABLE-5.

In the EMBODIMENTS 24 and 32, RebD and RebM were dissolved using γ- or β-cyclodextrins. γ-Cyclodextrin was used in an amount of 1:1, mol/mol to the glycosides, and β-cyclodextrin—2 mol for 1 mol glycosides. In some embodiments, β-cyclodextrin was converted to the mixture of α-, β- and γ-cyclodextrins by treatment of 10% water solution with CGTase at 65° C. for 12 hrs prior mixing with starch.

Embodiment 33

Low-Calorie Orange Juice Drink

Orange concentrate (35%), citric acid (0.38%), ascorbic acid (0.05%), sodium benzoate (0.02%); orange red color (0.01%), orange flavor (0.20%), and a sweetener (0.06%), obtained according to the EMBODIMENTS 1, 8, 9, 16, 24, and 32; however, other samples also can be used, were blended and dissolved completely in water (up to 100%) and pasteurized.

The sensory evaluations of the samples are summarized in the TABLE 6. All the samples with low-content of non-modified glycosides and deeply glycosylated derivatives show excellent sweetening and can be used for the preparation of good quality low-calorie orange juice.

TABLE 6

| Sample | Comments | | |
|---|---|---|---|
| | Flavor | Aftertaste | Mouth feel |
| No. 1 | Sweet, rounded and balanced flavor | Sweet, slightly bitter notes | Quite full |
| No. 8 | Sweet, rounded and balanced flavor | Clean, no bitterness and aftertaste | Full |
| No. 9 | Sweet, rounded and balanced flavor | Sweet, slightly bitter notes | Quite full |
| No. 16 | High quality sweetness | Clean, no bitterness and aftertaste | Full |
| No. 24 | High quality sweetness, pleasant, taste close to sucrose rounded and balanced flavor | Clean, no bitterness and aftertaste | Full |
| No. 32 | High quality sweetness, pleasant, taste close to sucrose rounded and balanced flavor | Clean, no bitterness and aftertaste | Full |

By the same way can be prepared juices from other fruits, such as apples, lemons, apricots, cherries, pineapples, etc.

Embodiment 34

Low-Calorie Carbonated Drink

The formula for the beverage was as below:

| Ingredients | Quantity, % |
|---|---|
| Cola flavor | 0.340 |
| Phosphoric acid (85%) | 0.100 |
| Sodium citrate | 0.310 |
| Sodium benzoate | 0.018 |
| Citric acid | 0.018 |
| Sweetener | 0.030 |
| Carbonated water | to 100 |

The beverages prepared with different sweeteners were given to 10 judges for comparison. TABLE 7 shows the results.

TABLE 7

| Taste attribute | Number of panelists | | | | | |
|---|---|---|---|---|---|---|
| | Sample No. 1 | Sample No. 8 | Sample No. 9 | Sample No. 16 | Sample No. 24 | Sample No. 32 |
| Bitter taste | 1 | 0 | 1 | 0 | 0 | 0 |
| Astringent taste | 1 | 0 | 0 | 0 | 0 | 0 |

TABLE 7-continued

| Taste attribute | Sample No. 1 | Sample No. 8 | Sample No. 9 | Sample No. 16 | Sample No. 24 | Sample No. 32 |
|---|---|---|---|---|---|---|
| | | | Number of panelists | | | |
| Aftertaste | 3 | 0 | 2 | 0 | 0 | 0 |
| Quality of sweet taste | Sweet, slight cooling aftertaste (3 of the 10 judges) | Clean (10 of the 10 judges) | Lingering sweet taste. Slight cooling aftertaste | Clean (10 of the 10 judges) | Clean (10 of the 10 judges) | Clean (10 of the 10 judges) |
| Overall | Acceptable (7 of the 10 judges) | Excellent (10 of the 10 judges) | Good (8 of the 10 judges) | Excellent (10 of the 10 judges) | Excellent (10 of the 10 judges) | Excellent (10 of the 10 judges) |

The above results show that the beverages prepared using the Samples No. 8, 16, 24, and 32 are outstanding in aftertaste and possess good organoleptic characteristics.

Embodiment 35

Ice Lemon Tea
The formula for the beverage was as below:

| Ingredients | Quantity, % |
|---|---|
| Sweetener | 0.08 |
| Sodium benzoate | 0.02 |
| Citric acid | 0.27 |
| Ascorbic acid | 0.01 |
| Tea extract | 0.03 |
| Lemon flavor | 0.10 |
| Water | to 100 |

All ingredients were blended and dissolved in the water and pasteurized.

The products with all the samples, such as No. 1, No. 8, No. 9, 16, 24, and 32 possessing an excellent taste and flavor. However, the Samples No. 8, 16, 24, and 32 provided somewhat better taste profile because of fuller mouthfeel.

Embodiment 36

Yogurt
In 5 kg of defatted milk 4.0 grams of sweetener, prepared according to EMBODIMENTS 2, 3, 4 or 5, were dissolved, and after pasteurizing at 82° C. for 20 minutes, the milk was cooled to 40° C. A starter in amount of 150 grams was added and the mixture was incubated at 37° C. for 6 hours. Then, the fermented mass was maintained at 10-15° C. for 12 hours.

The product with Samples No. 1, No. 8, No. 9, No. 16, No. 24, and No. 32 is a low-calorie and low-cariogenic yoghurt without foreign taste and odor.

It is to be understood that the foregoing descriptions and specific embodiments shown herein are merely illustrative of the best mode of the application and the principles thereof, and that modifications and additions may be easily made by those skilled in the art without departing for the spirit and scope of the application, which is therefore understood to be limited only by the scope of the appended claims.

REFERENCES

Starratt A. N., Kirby C. W., Pocs R., Brandle J. E. (2002) Rebaudioside F, a diterpene glycoside from *Stevia rebaudiana. Phytochemistry.* 59. 367-370.

Kohda H, Kasi R., Yamasaki K, Murakami K, Tanaka O (1976) New sweet diterpene glucoside from *Stevia rebaudiana. Phytochemistry* (Oxford). 15. 981-983.

Chaturvedula V. S. P., Upreti M. and I. Prakash (2011) Structures of the novel α-glucosyl linked diterpene glycosides from *Stevia rebaudiana. Carb. Res.* 346 (13). 2034-2038.

Fukunaga, Y, Miyata, T., Nakayasu, N., Mizutani, K., Tanaka, O. R. (1989) Enzymic transglucosylation products of stevioside: separation and sweetness evaluation. Agriculture and Biological Chemistry. 53. 1603-1607.

Lobov S. V., Jasai R., Ohtani K., Tanaka O. Yamasaki K. (1991) Enzymatic production of sweet stevioside derivatives: transglycosylation by glucosidases. Agric. Biol. Chem. 55: 2959-2965.

Kitahata S., Ishikawa S., Miyata T., Tanaka O. (1989) Production of rubusoside derivatives by transglycosylation of various β-galactosidase. Agric. Biol. Chem. 53: 2923-2928.

Yamamoto K., Yoshikawa K., Okada S. (1994) Effective production of glucosyl-stevioside by α-1,6-transglucosylation of dextran dextranase. Biosci. Biotech. Biochem. 58: 1657-1661.

Tanaka O. (1997) Improvement of taste of natural sweeteners. Pure & Appl. Chem. 69. 4. 675-683.

Miyata T., Sawaguchi Y, Aikawa M. (1991a) Highly sweet Stevia sweetener and its production. Japan Patent 03-83558.

Miyata T., Sawaguchi Y, Aikawa M. (1991b) Highly sweet tranglycosylated Stevia sweetener and the method of production of this product. Japan Patent 03-262458.

Cai Y., Chjen K., Fang Y., Li W., Wang L., Xia Y, Zhang Z. (2010) Chines Pat Appl CN201010131126.

Jaitak V., Kumar K. V., Kumar N. B., Singh B., Savergave L. S., Jogdand V. V., Nene S. (2009) Simple and efficient enzymatic transglycosylation of stevio side by β-cyclodextrin glucanotransferase from *Bacillus firmus*. Biotechnol. Letters. 31 (9). 1415-1420.

Jaitak V. (2010) Chemical Investigation of Medicinal and Aromatic Plants and Synthetic Modifications of Organic Molecules by Chemical and Enzymatic Processes. PhD Thesis. Institute of Himalayan Bioresource Technology. India. 269pp.

Kasai R., Kaneda N., Tanaka O., Yamasaki K., Sakamoto I., Morimoto K., Okada S., Kitahata S., Furukawa H. (1981) Sweet diterpene-glycosides of leaves of *Stevia rebaudiana Bertoni*. Synthesis and structure—sweetness relationship of rebaudiosides-A, D, E and their related glycosides. Nippon Kagaku kaishi. 5. 726-735.

Kitahata S. (2001) Carrent industrial production and application of saccharides in Japan. Kasai Research Institute. 202p.

Toyo Sugar Refining Co., Ltd., Nippon Paper Chemicals Co., Ltd. (2011) GRAS Assessment of α-glucosylated steviol glycosides.

What is claimed is:

1. A process for producing α-1.4-glucosylated steviol glycosides, said process comprising:
   providing a steviol glycoside and a donor of glucosyl residues, wherein both are mixed in a predetermined ratio to obtain a reaction solution,
   adding CGTase for transglucosylation of steviol glycosides to the reaction solution; whereby the reaction solution is incubated at a predetermined temperature for a predetermined period;
   passing the reaction solution through a chromatographic column packed with sufficient amount of specific polar macroporous polymeric adsorbent;
   washing the column to remove impurities; and
   eluting adsorbed non-modified steviol glycosides and glycosylated steviol glycosides with an organic solvent solution; and
   removing the organic solvent, concentrating, and drying to produce a purified sweetener composition comprising α-1.4-glucosylated steviol glycosides;
   the donor of glucosyl residues is partially hydrolyzed starch, maltooligosaccharides, or a mixture of partially hydrolyzed starch and maltooligosaccharides;
   the partially hydrolyzed starch is prepared by:
   suspending predetermined quantity of starch in distilled or deionized water to obtain a starch suspension; and
   adding CGTase for starch liquefaction to the starch suspension and incubating the suspension at a temperature in a range of 75-80° C. for a period in a range of 0.5-2 hours;
   the partially hydrolyzing starch further comprises:
   cooling the liquefied starch mixture down to 50-55° C.; and
   adding pullulanase in an amount in the range of 0.3-0.9 units/gram starch; whereby the reaction continues for a period of 3-8 hours.

2. The process of claim 1, wherein the steviol glycosides is represented by the following formula I:

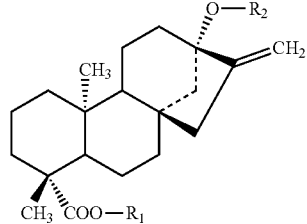

(formula I)

wherein the compound name and corresponding $R_1$ and $R_2$ structures are listed hereinbelow:

| Compound name | R1 (C-19) | R2 (C-13) |
|---|---|---|
| 1. Steviol | H | H |
| 2. Steviolmonoside | H | β-Glc |
| 3. Rubusoside | β-Glc | β-Glc |
| 4. Steviolbioside | H | β-Glc-β-Glc(2→1) |
| 5. Stevioside | β-Glc | β-Glc-β-Glc(2→1) |
| 6. Rebaudioside A | β-Glc | β-Glc-β-Glc(2→1)<br>\|<br>β-Glc(3→1) |
| 7. Rebaudioside B | H | β-Glc-β-Glc(2→1)<br>\|<br>β-Glc(3→1) |
| 8. Rebaudioside C | β-Glc | β-Glc-α-Rha(2→1)<br>\|<br>β-Glc(3→1) |
| 9. Rebaudioside D | β-Glc-β-Glc(2→1) | β-Glc-β-Glc(2→1)<br>\|<br>β-Glc(3→1) |
| 10. Rebaudioside E | β-Glc-β-Glc(2→1) | β-Glc-β-Glc(2→1) |
| 11. Rebaudioside F | β-Glc | β-Glc-β-Xyl(2→1)<br>\|<br>β-Glc(3→1) |
| 12. Dulcoside A | β-Glc | β-Glc-α-Rha(2→1) |
| 13. Dulcoside B | H | β-Glc-α-Rha(2→1)<br>\|<br>β-Glc(3→1) |
| 14. Rebaudioside G | β-Glc | β-Glc-β-Glc(3→1) |
| 15. Rebaudioside I | β-Glc-β-Glc(3→1) | β-Glc-β-Glc(2→1)<br>\|<br>β-Glc(3→1) |

-continued

| Compound name | R1 (C-19) | R2 (C-13) |
|---|---|---|
| 16. Rebaudioside H | β-Glc | β-Glc-α-Rha(2→1)-β-Glc(3→1)<br>    |<br>β-Glc(3→1) |
| 17. Rebaudioside L | β-Glc | β-Glc-β-Glc(2→1)<br>    |   } β-Glc(6→1)<br>β-Glc(3→1) |
| 18. Rebaudioside K | β-Glc-β-Glc(2→1) | β-Glc-α-Rha(2→1)<br>    |<br>β-Glc(3→1) |
| 19. Rebaudioside J | β-Glc-α-Rha(2→1) | β-Glc-β-Glc(2→1)<br>    |<br>β-Glc(3→1) |
| 20. Rebaudioside M | β-Glc-β-Glc(2→1)<br>    |<br>β-Glc(3→1) | β-Glc-β-Glc(2→1)<br>    |<br>β-Glc(3→1) |
| 21. Rebaudioside N | β-Glc-α-Rha(2→1)<br>    |<br>β-Glc(3→1) | β-Glc-β-Glc(2→1)<br>    |<br>β-Glc(3→1) |
| 22. Rebaudioside O | β-Glc-α-Rha(2→1)-<br>β-Glc(3→1) | β-Glc-β-Glc(2→1).<br>    |<br>β-Glc(3→1) |

3. The process of claim 2, wherein the steviol glycoside is selected from the group consisting of stevioside, Rebaudioside A (RebA), Rebaudioside B (RebB), Rebaudioside C (RebC), Rebaudioside D (RebD), Rebaudioside E (RebE), Rebaudioside F (RebF), Rebaudioside M (RebM), dulcoside A, steviolbioside, and rubusoside.

4. The process of claim 1, wherein the starch suspension contains starch in a concentration in a range of 20-40%.

5. The process of claim 4, wherein the starch suspension contains starch in a concentration in a range of 25-33%.

6. The process of claim 1, wherein the CGTase for starch liquefaction is in the range of 1-5 units/gram of starch.

7. The process of claim 6, wherein the CGTase for starch liquefaction is in the range of 2-3 units/gram of starch.

8. The process of claim 1, wherein the liquefied starch mixture has a dextrose equivalent of 10-25.

9. The process of claim 8, wherein the liquefied starch mixture has a dextrose equivalent of 12-16.

10. The process of claim 1, wherein when the partially hydrolyzed starch is used, the starch solution is used without inactivation of CGTase and pullulanase.

11. The process of claim 1, wherein the predetermined ratio of steviol glycosides with the donors of glucosyl residues is in the range of 0.1-1.0 w/w.

12. The process of claim 11, wherein the predetermined ratio of steviol glycosides with the donors of glucosyl residues is in the range of 0.5-1.0 w/w.

13. The process of claim 1, wherein the CGTase for transglucosylation of steviol glycosides is in an amount in a range of 7-15 units/gram of starch; the predetermined temperature is in a range of 50-75° C.; and the predetermined period is in a range of 18-72 hours.

14. The process of claim 13, wherein the CGTase for transglucosylation of steviol glycosides is in an amount in a range of 8-11 units/gram of starch; the predetermined temperature is in a range of 50-75° C.; and the predetermined period is in a range of 18-72 hours.

15. The process of claim 1, wherein after the reaction with the added CGTase for transglucosylation of steviol glycosides is being carried out for 1-2 hours, a miscible or immiscible organic solvent is added to the reaction mixture in an amount to reach a final concentration in a range of 2-20 v/v %, and the reaction continues for another 18-72 hours at 50-75° C.

16. The process of claim 15, wherein the organic solvent is ethanol, methanol or isopropanol.

17. The process of claim 15, wherein after the reaction with the added CGTase for transglucosylation of steviol glycosides is being carried out for 1-2 hours, a miscible or immiscible organic solvent is added to the reaction mixture in an amount to reach a final concentration in a range of 7-15%, and the reaction continues for another 18-72 hours at 50-75° C.

18. The process of claim 15, wherein when the partially hydrolyzed starch is used, the starch solution is used with inactivation of CGTase, after inactivation of CGTase, the reaction solution is treated with a β-amylase for 5-7 hours at 45-50° C.; wherein the β-amylase is in a range of 5-15 units per gram of total glycosides.

19. The process of claim 1, wherein the polar macroporous polymeric adsorbent is Diaion HP-20, Amberlite XAD-7 and Amberlite XAD-4 or LX-T28.

20. The process of claim 1, wherein the washing includes at least three volumes of RO water, at least two volumes of 0.3-0.5% of NaOH, at least three volumes of RO water, at least two volumes of 8-10% ethanol, at least two volumes of 0.3-0.5% HCl, and then with RO water to pH 5.5-7.0.

21. The process of claim 1, wherein the eluting is with 2-3 volumes of 52-70% ethanol.

22. The process of claim 1, wherein the partially hydrolyzed starch is prepared by:
    suspending predetermined quantity of starch in distilled or deionized water to obtain a starch suspension; and
    adding CGTase for starch liquefaction to the starch suspension and incubating the suspension at a temperature in a range of 75-80° C. for a period in a range of 0.8-1.2 hours.

23. The process of claim 1, wherein the partially hydrolyzing starch further comprises:
- cooling the liquefied starch mixture down to 50-55° C.; and
- adding pullulanase in an amount in the range of 0.5-0.7 units/gram starch; whereby the reaction continues for a period of 4-6 hours.

* * * * *